US010369156B2

(12) United States Patent
Rodgers et al.

(10) Patent No.: US 10,369,156 B2
(45) Date of Patent: Aug. 6, 2019

(54) COMPOSITIONS FOR THE TREATMENT OF HYPERTENSION

(71) Applicants: The George Institute for Global Health, Newtown, Sydney, NSW (AU); The University of Sydney, Sydney, NSW (AU)

(72) Inventors: Anthony Rodgers, Newtown (AU); Clara Chow, Sydney (AU)

(73) Assignees: THE GEORGE INSTITUTE FOR GLOBAL HEALTH, Newtown, Sydney, NSW (AU); THE UNIVERSITY OF SYDNEY, Sydney, NSW (AU)

( * ) Notice: Subject to any disclaimer, the term of this patent is extended or adjusted under 35 U.S.C. 154(b) by 0 days.

(21) Appl. No.: 15/352,425

(22) Filed: Nov. 15, 2016

(65) Prior Publication Data
US 2018/0133227 A1 May 17, 2018

(51) Int. Cl.
A61K 31/547 (2006.01)
A61K 31/549 (2006.01)
A61K 9/00 (2006.01)
A61K 31/138 (2006.01)
A61K 31/165 (2006.01)
A61K 31/4035 (2006.01)
A61K 31/404 (2006.01)
A61K 31/4184 (2006.01)
A61K 31/4422 (2006.01)
A61K 9/48 (2006.01)

(52) U.S. Cl.
CPC .......... *A61K 31/549* (2013.01); *A61K 9/0053* (2013.01); *A61K 31/138* (2013.01); *A61K 31/165* (2013.01); *A61K 31/404* (2013.01); *A61K 31/4035* (2013.01); *A61K 31/4184* (2013.01); *A61K 31/4422* (2013.01); *A61K 9/48* (2013.01)

(58) Field of Classification Search
None
See application file for complete search history.

(56) References Cited

U.S. PATENT DOCUMENTS

| 2004/0198789 | A1 | 10/2004 | Leonardi et al. |
| 2005/0187262 | A1 | 8/2005 | Grogan et al. |
| 2007/0191438 | A1* | 8/2007 | Rohrer .............. A61K 31/00 514/359 |
| 2012/0115854 | A1 | 5/2012 | Shetty et al. |
| 2013/0210778 | A1 | 8/2013 | Wald et al. |

FOREIGN PATENT DOCUMENTS

| CN | 101450211 A | 6/2009 |
| CN | 101966190 A | 2/2011 |
| CN | 102225203 A | 10/2011 |
| CN | 106310278 A | 1/2017 |
| EP | 1272220 B1 | 5/2006 |
| EP | 2575808 A1 | 4/2013 |
| WO | WO-2007098390 A2 | 8/2007 |
| WO | WO-2007146900 A2 | 12/2007 |
| WO | WO-2009026517 A2 | 2/2009 |
| WO | WO-2011149438 A1 | 12/2011 |
| WO | WO-2014114627 A1 | 7/2014 |
| WO | WO-2018091967 A1 | 5/2018 |
| WO | WO-2018138578 A1 | 8/2018 |

OTHER PUBLICATIONS

Mahmud et al (Hypertension 49:272-275, 2007).*
Spinier et al (available online at www.formularyjournal.com, Jun. 1, 2006).*
Neutel et al (J of Renin-Angiotensin Aldosteron System 6:84-89, 2005).*
Skoularigis et al (Am J Hyerptens 8:1046-1050, 1995—Abstract only).*
Berge et al. Pharmaceutical Salts. Journal of Pharmaceutical Sciences 66(1):1-19 (Jan. 1977).
Kenward et al. An improved approximation to the precision of fixed effects from restricted maximum likelihood. Computational Statistics & Data Analysis 53(7):2583-2595 (2009).
Kenward et al. The use of baseline covariates in crossover studies. Biostatistics 11(1):1-17 (2010).
Law et al. Lowering blood pressure to prevent myocardial infarction and stroke: a new preventive strategy. Health Technology Assessment 7(31):1-106 (2003).
Law et al. Value of low dose combination treatment with blood pressure lowering drugs: analysis of 354 randomised trials. BMJ 326(7404):1427 (2003).
Liu et al. Should baseline be a covariate or dependent variable in analyses of change from baseline in clinical trials? Stat Med 28(20):2509-2530 (2009).
Mahmud et al. Low-dose quadruple antihypertensive combination: more efficacious than individual agents—a preliminary report. Hypertension 49:272-275 (2007).
Wald et al. Combination therapy versus monotherapy in reducing blood pressure: meta-analysis on 11,000 participants from 42 trials. Am J Med 122(3):290-300 (2009).
Wald et al. Randomized Polypill crossover trial in people aged 50 and over. PLoS One 7(7):e41297 (2012).
Co-pending U.S. Appl. No. 15/919,923, filed Mar. 13, 2018.
O'Brien et al. Ambulatory Blood Pressure Measurement. What Is the International Consensus? Hypertension 62(6):988-994 (2013).
Pinto et al. Lessons from rat models of hypertension: from Goldblatt to genetic engineering. Cardiovascular Res 39(1):77-88 (1998).

(Continued)

*Primary Examiner* — Craig D Ricci
(74) *Attorney, Agent, or Firm* — Wilson Sonsini Goodrich & Rosati

(57) ABSTRACT

Provided herein are pharmaceutical compositions that are useful for the treatment of hypertension comprising an angiotensin II receptor blocker, a diuretic, a calcium channel blocker, and a beta-blocker, wherein the dose of each component is below the lowest dose approved for the treatment of hypertension for the component.

6 Claims, 2 Drawing Sheets

(56) References Cited

OTHER PUBLICATIONS

Drug Dosage. https://www.drugs.com/dosage/ (3 pgs.) (Accessed Apr. 2018).
PCT/IB2017/001524 International Search Report and Written Opinion dated Apr. 17, 2018.
PCT/IB2018/000083 International Search Report and Written Opinion dated Apr. 24, 2018.
Fishbane et al. Iron deficiency in non-dialysis chronic kidney disease. Kidney Int 75:752-754 (2008).
Emc+ Compendium. Latest Medicine Updates.https://www.medicines.org.uk/emc (2 pgs.) (Accessed Apr. 2018).
Huo et al. Effect of Simvastatin on Ankle Brachial Index in Middle and Old Age Patients with Hypertension. China Pharmacy 24(40):3795-3796 (2013) (English Abstract).
Kuriyama et al. Renoprotective effect of triple therapy with low-dose angiotensis receptor blocker, low-dose diuretic and Ca-antagonist in hypertensive type-2 diabetic patients with overt nephropathy. Japanese Journal of Nephrology 45:367-371 (2003) (English Abstract).
RxList. https://www.rxlist.com(5 pgs.) (Accessed Apr. 2018).
Tandon et al. Antihypertensive drug prescription patterns, rationality, and adherence to Joint National Committee-7 hypertension treatment guidelines among Indian postmenopausal women. J Midlife Health 5(2):78--83 (2014).
Triple Therapy Prevention of Recurrent Intracerebral Disease EveNts Trial (TRIDENT). Available at https://clinicaltrials.gov/ct2/show/record/NCT02699645. First posted Mar. 4, 2016 (16 pgs).
Diabetes Educational Services. Available at https://diabetesed.net/page/files/Antihypertensive-Meds-2012.pdf (3 pgs.) (2012).
Huffman et al. Low-Dose Combination Blood Pressure Pharmacotherapy to Improve Treatment Effectiveness, Safety and Efficiency. JAMA 320(6):552-554 (2018).
Salam et al. TRIple pill vs Usual care Management for Patients with mild-to-moderate Hypertension (TRIUMPH): Study protocol. Am Heart J. 167(2):127-132 (2014).
Triple Therapy Prevention of Recurrent Intracerebral Disease EveNts Trial (TRIDENT). Available at https://clinicaltrials.gov/ct2/show/record/NCT02699645. First posted Mar. 4, 2016 (Latest version Oct. 2, 2018) (9 pgs).
U.S. Appl. No. 15/919,923 Office Action dated Aug. 15, 2018.
U.S. Appl. No. 15/919,923 Office Action dated Nov. 15, 2018.
Webster et al. Fixed Low-Dose Triple Combination Antihypertensive Medication vs Usual Care for Blood Pressure Control in Patients With Mild to Moderate Hypertension in Sri Lanka: A Randomized Clinical Trial. JAMA 320(6):566-579 (2018).
Webster. Protocol changes to the TRIUMPH study. Am Heart J 191:e1 (2017).
Beall et al. Could patents interfere with the development of a cardiovascular polypill? J Trans! Med 14:242 (2016).

\* cited by examiner

COMPOSITIONS FOR THE TREATMENT OF HYPERTENSION

BACKGROUND OF THE DISCLOSURE

High blood pressure, also known as hypertension, is a leading cause of preventable morbidity and mortality and it is well established that treatments that lower blood pressure (BP) are beneficial. However, despite the plethora of blood pressure lowering medicines available, many patients continue to have poor blood pressure control as evidenced by multiple large-scale population studies. Contributing factors for poor blood pressure control include poor adherence, complex guidelines recommending multiple up-titration steps, and treatment inertia. Furthermore, the majority of treated patients receive only monotherapy, which has limited potency even at high doses where side effects are increased and tolerability reduced. Accordingly, there exists a need for new treatments for lowering high blood pressure that are efficacious and tolerable.

SUMMARY OF THE DISCLOSURE

Provided herein is a pharmaceutical composition comprising
  (a) an angiotensin II receptor blocker;
  (b) a diuretic;
  (c) a calcium channel blocker; and
  (d) a beta-blocker;
wherein the dose of each (a), (b), (c), and (d) is from about 20% to about 60% of the lowest hypertension therapeutic dose (LHTD) for each of the (a), (b), (c), and (d).

In some embodiments, the dose of each (a), (b), (c), and (d) is from about 40% to about 60% of the lowest hypertension therapeutic dose (LHTD) for each of the (a), (b), (c), and (d). In some embodiments, the pharmaceutical composition is essentially free of a lipid-regulating agent, platelet function altering agent, a serum homocysteine lowering agent, or a combination thereof.

In some embodiments, the diuretic is a thiazide diuretic, and the thiazide diuretic is altizide, bendroflumethiazide, chlorothiazide, cyclopenthiazide, cyclothiazide, epitizide, hydrochlorothiazide, hydroflumethiazide, mebutizide, methyclothiazide, polythiazide, trichlormethiazide, or the pharmaceutically acceptable salt or hydrate thereof.

In some embodiments, the dose of the thiazide diuretic is about 50% of the lowest hypertension therapeutic dose (LHTD) for the thiazide diuretic. In some embodiments, the thiazide diuretic is hydrochlorothiazide, and the dose of the hydrochlorothiazide is about 6.25 mg.

In some embodiments, the diuretic is a thiazide-like diuretic, and the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof. In some embodiments, the dose of the thiazide-like diuretic is about 50% of the lowest hypertension therapeutic dose (LHTD) for the thiazide-like diuretic. In some embodiments, the thiazide-like diuretic is indapamide, and the dose of the indapamide is about 0.625 mg. In some embodiments, the thiazide-like diuretic is chlorthalidone, and the dose of the chlorthalidone is about 12.5 mg.

In some embodiments, the dose of the calcium channel blocker is about 50% of the lowest hypertension therapeutic dose (LHTD) for the calcium channel blocker. In some embodiments, the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof. In some embodiments, the calcium channel blocker is amlodipine besylate, and the dose of amlodipine besylate is about 1.25 mg.

In some embodiments, the dose of the beta-blocker is about 50% of the lowest hypertension therapeutic dose (LHTD) for the beta-blocker. In some embodiments, the beta-blocker is acebutolol, atenolol, betaxolol, bisoprolol, carteolol, esmolol, penbutolol, metoprolol, nadolol, nebivolol, pindolol, sotalol, propranolol, carvedilol, labetalol, timolol, esmolol, celiprolol, oxprenolol, levobunolol, practolol, metipranolol, landiolol, bopindolol, pronethalol, butaxamine, bevantolol, tertatolol, arotinolol, levobetaxolol, befunolol, amosulalol, tilisolol, or the pharmaceutically acceptable salt or hydrate thereof. In some embodiments, the beta-blocker is atenolol, and the dose of atenolol is about 12.5 mg. In some embodiments, the beta-blocker is bisoprolol fumarate, and the dose of bisoprolol fumarate is about 2.5 mg.

In some embodiments, dose of the angiotensin II receptor blocker is about 50% of the lowest hypertension therapeutic dose (LHTD) for the angiotensin II receptor blocker. In some embodiments, the angiotensin II receptor blocker is irbesartan, telmisartan, valsartan, candesartan, eprosartan, olmesartan, azilsartan, losartan, or the pharmaceutically acceptable salt or hydrate thereof. In some embodiments, the angiotensin II receptor blocker is irbesartan, and the dose of the irbesartan is about 37.5 mg. In some embodiments, the angiotensin II receptor blocker is telmisartan, and the dose of the telmisartan is about 10 mg.

In some embodiments, the angiotensin II receptor blocker is irbesartan, the diuretic is hydrochlorothiazide, the calcium channel blocker is amlodipine besylate, and the beta blocker is atenolol. In some embodiments, the dose of irbesartan is about 30 mg to about 45 mg, the dose of hydrochlorothiazide is about 5 mg to about 7.5 mg, the dose of amlodipine besylate is about 1 mg to about 1.5 mg, and the dose of atenolol is about 10 mg to about 15 mg.

In some embodiments, the angiotensin II receptor blocker is irbesartan, the diuretic is indapamide, the calcium channel blocker is amlodipine besylate, and the beta-blocker is bisoprolol fumarate. In some embodiments, the dose of irbesartan is about 30 mg to about 45 mg, the dose of indapamide is about 0.5 mg to about 0.75 mg, the dose of amlodipine besylate is about 1 mg to about 1.5 mg, and the dose of bisoprolol fumarate is about 2 mg to about 3 mg.

In some embodiments, (a), (b), (c) and (d) are provided in one formulation. In some embodiments, the pharmaceutical composition is suitable for oral administration.

Also provided herein in another aspect is a method of treating hypertension in a subject in need thereof comprising administering the pharmaceutical composition comprising.
  (a) an angiotensin II receptor blocker;
  (b) a diuretic;
  (c) a calcium channel blocker; and
  (d) a beta-blocker;
wherein the dose of each (a), (b), (c), and (d) is from about 20% to about 60% of the lowest hypertension therapeutic dose (LHTD) for each of the (a), (b), (c), and (d).

In some embodiments, the treatment results in a reduction of systolic blood pressure (SBP) of about 10 mmHg or greater. In some embodiments, the treatment results in a reduction of diastolic blood pressure (DBP) of about 5 mmHg or greater. In some embodiments, the treatment is the initial or first-line treatment of hypertension.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
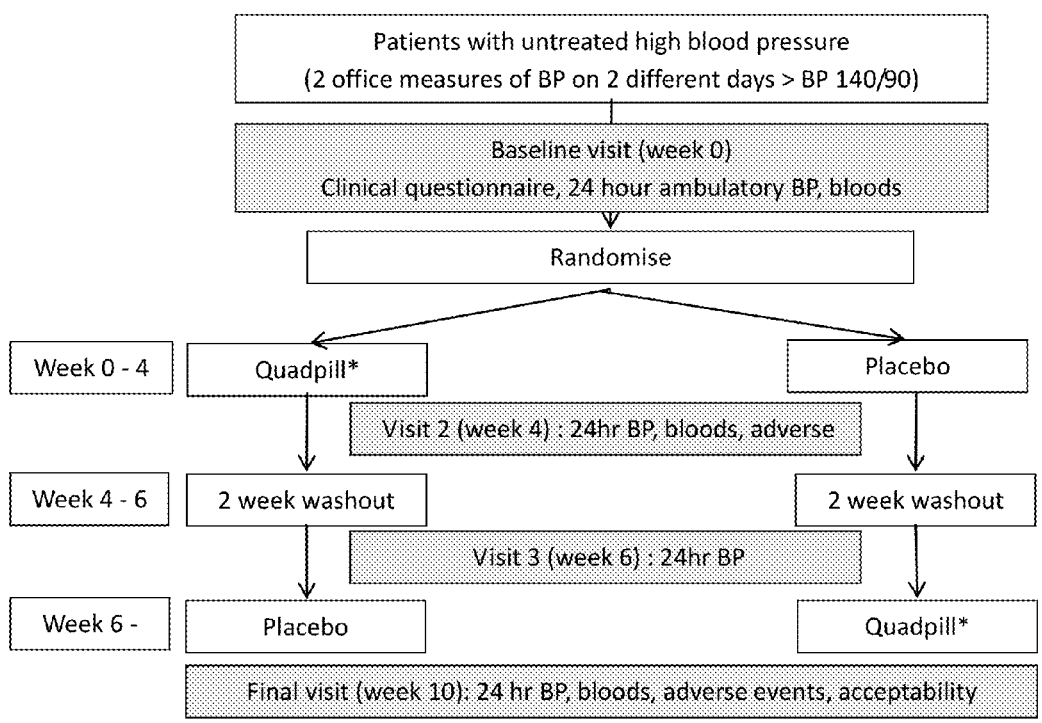
FIG. 1 shows the study design of Example 1.

Provided herein are pharmaceutical compositions for the treatment of hypertension comprising an angiotensin II receptor blocker, a diuretic, a calcium channel blocker, and a beta-blocker, wherein the dose of each component is below the lowest dose approved for the treatment of hypertension. The present disclosure recognizes the technical effects of low-dose combination therapy set forth herein, including but not limited to, the use of low-doses to avoid or ameliorate side effects while retaining or improving benefits, the synergistic therapeutic benefits of certain drug combinations, the early introduction of combination therapy to improve therapeutic effects, etc. Described herein are low-dose combination compositions for the treatment of hypertension, including the initial or first-line treatment of hypertension.

Certain Terminology

As used herein and in the appended claims, the singular forms "a," "and," and "the" include plural referents unless the context clearly dictates otherwise. Thus, for example, reference to "an agent" includes a plurality of such agents, and reference to "the composition" includes reference to one or more compositions (or to a plurality of compositions) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 10% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Pharmaceutically acceptable salt" as used herein includes both acid and base addition salts. In some embodiments, the pharmaceutically acceptable salt of any one of the compounds described herein is the form approved for use by the US Food and Drug Administration. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "hydrates" are compounds that contain either stoichiometric or non-stoichiometric amounts of water, and, in some embodiments, are formed during the process of crystallization with water. Hydrates are meant to include the hydrates of any one of the compounds described herein that is approved for use by the US Food and Drug Administration.

The term "acceptable" with respect to a formulation, composition or ingredient, as used herein, means having no persistent detrimental effect on the general health of the subject being treated.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Quadruple Compositions

Described herein are pharmaceutical compositions comprising (a) an angiotensin II receptor blocker; (b) a diuretic; (c) a calcium channel blocker; and (d) a beta-blocker; wherein the dose of each (a), (b), (c), and (d) is from about 20 to about 60% of the lowest hypertension therapeutic dose (LHTD) for each of the (a), (b), (c), and (d). In some embodiments, the dose of each (a), (b), (c), and (d) is about 40% to about 60% of the lowest hypertension therapeutic dose (LHTD) for each of the (a), (b), (c), and (d). In some embodiments, the dose of each (a), (b), (c), and (d) is about 50% of the lowest hypertension therapeutic dose (LHTD) for each of the (a), (b), (c), and (d).

Also, described herein are pharmaceutical compositions consisting essentially of (a) an angiotensin II receptor blocker; (b) a diuretic; (c) a calcium channel blocker; and (d) a beta-blocker; wherein the dose of each (a), (b), (c), and (d) is from about 20 to about 60% of the lowest hypertension therapeutic dose (LHTD) for each of the (a), (b), (c), and (d). In some embodiments, the dose of each (a), (b), (c), and (d) is about 40% to about 60% of the lowest hypertension therapeutic dose (LHTD) for each of the (a), (b), (c), and (d). In some embodiments, the dose of each (a), (b), (c), and (d) is about 50% of the lowest hypertension therapeutic dose (LHTD) for each of the (a), (b), (c), and (d).

In some embodiments, the pharmaceutical compositions disclosed herein achieve a significant blood pressure reduction in a subject with modestly elevated blood pressure. In some embodiments, the pharmaceutical compositions disclosed herein achieve a significant blood pressure reduction in a subject with modestly elevated blood pressure with minimum, insignificant or no side effects.

Lipid-Regulating Agent

In some embodiments, the pharmaceutical compositions disclosed herein are essentially free of a lipid-regulating agent, a platelet function altering agent, a serum homocysteine lowering agent, or a combination thereof.

In some embodiments, the pharmaceutical compositions disclosed herein are essentially free of a lipid-regulating agent. In some embodiments, the lipid-regulating agent is a 3-hydroxy-3-methylglutaryl coenzyme A (HMG CoA) reductase inhibitor, also called a statin. In some embodiments, the lipid-regulating agent is atorvastatin, simvastatin, cerivastatin, fluvastatin, or pravastatin. In some embodiments, the lipid-regulating agent is atorvastatin or simvastatin. In some embodiments, the lipid-regulating agent is atorvastatin. In some embodiments, the lipid-regulating agent is simvastatin.

Platelet Function Altering Agent

In some embodiments, the pharmaceutical compositions disclosed herein are essentially free of a platelet function altering agent. In some embodiments, the platelet function altering agent is aspirin, ticlopidine, dipyridamole, clopidogrel. In some embodiments, the platelet function altering agent is a glycoprotein IIb/IIIa receptor inhibitor, such as abciximab. In some embodiments, the platelet function altering agent is a non-steroidal anti-inflammatory drug, such as ibuprofen. In some embodiments, the platelet function altering agent is aspirin, ticlopidine, dipyridamole, clopidogrel, abciximab, or ibuprofen. In some embodiments, the platelet function altering agent is aspirin.

Serum Homocysteine Lowering Agent

In some embodiments, the pharmaceutical compositions disclosed herein are essentially free of a serum homocysteine lowering agent. In some embodiments, the serum homocysteine lowering agent is folic acid, vitamin B6, or vitamin B12, or a combination thereof. In some embodiments, the serum homocysteine lowering agent is folic acid.

Angiotensin II Receptor Antagonist/Blocker

As used herein, angiotensin II receptor antagonists or blockers (ARBs) are compounds that modulate the action of angiotensin II by preventing angiotensin II from binding to angiotensin II receptors on the muscles surrounding blood vessels. In some embodiments, angiotensin II receptor blocker is losartan, valsartan, candesartan, eprosartan, irbesartan, telmisartan, or the pharmaceutically acceptable salt or hydrate thereof. In some embodiments, angiotensin II receptor blocker is losartan. In some embodiments, the angiotensin II receptor blocker is valsartan. In some embodiments, the angiotensin II receptor blocker is candesartan. In some embodiments, the angiotensin II receptor blocker is eprosartan. In some embodiments, the angiotensin II receptor blocker is irbesartan. In some embodiments, the angiotensin II receptor blocker is telmisartan.

Diuretics

As used herein, diuretics refer to compounds that increase urinary flow rate. Diuretics are classified by chemical structure (thiazide diuretics and thiazide like diuretics), site of action (such as loop diuretic) or pharmacologic effect (such as osmotic diuretics, carbonic anhydrase inhibitors, and potassium sparing diuretics).

In some embodiments, the pharmaceutical compositions disclosed herein comprise a thiazide diuretic. In some embodiments, the pharmaceutical compositions disclosed herein comprise a thiazide like diuretic. In some embodiments, the pharmaceutical compositions disclosed herein comprise a loop diuretic. In some embodiments, the pharmaceutical compositions disclosed herein comprise an osmotic diuretic. In some embodiments, the pharmaceutical compositions disclosed herein comprise a carbonic anhydrase inhibitor. In some embodiments, the pharmaceutical compositions disclosed herein comprise a potassium sparing diuretic.

Thiazide Diuretics

As used herein, thiazide diuretics refer to compounds that contain the benzothiadiazine molecular structure. In some embodiments, thiazide diuretics inhibit sodium and chloride reabsorption in the distal tubule of the kidney, which results in increased urinary excretion of sodium and water. Examples of thiazide diuretics include but are not limited to altizide, bendroflumethiazide, chlorothiazide, cyclopenthiazide, cyclothiazide, epitizide, hydrochlorothiazide, hydroflumethiazide, mebutizide, methyclothiazide, polythiazide, and trichlormethiazide. In some embodiments, the thiazide diuretic is altizide, bendroflumethiazide, chlorothiazide, cyclopenthiazide, cyclothiazide, epitizide, hydrochlorothiazide, hydroflumethiazide, mebutizide, methyclothiazide, polythiazide, trichlormethiazide, or the pharmaceutically acceptable salt or hydrate thereof. In some embodiments, the thiazide diuretic is altizide. In some embodiments, the thiazide diuretic is bendroflumethiazide. In some embodiments, the thiazide diuretic is chlorothiazide. In some embodiments, the thiazide diuretic is cyclopenthiazide. In some embodiments, the thiazide diuretic is cyclothiazide. In some embodiments, the thiazide diuretic is epitizide. In some embodiments, the thiazide diuretic is hydrochlorothiazide. In some embodiments, the thiazide diuretic is hydroflumethiazide. In some embodiments, the thiazide diuretic is mebutizide. In some embodiments, the thiazide diuretic is methyclothiazide. In some embodiments, the thiazide diuretic is polythiazide. In some embodiments, the thiazide diuretic is trichlormethiazide.

Thiazide-Like Diuretics

As used herein, a thiazide-like diuretic is a sulfonamide diuretic that has similar physiological properties to a thiazide diuretic, but does not have the chemical properties of a thiazide (i.e. does not have the benzothiadiazine core). Examples of thiazide-like diuretics include but are not limited to quinethazone, clopamide, chlorthalidone, mefruside, clofenamide, metolazone, meticrane, xipamide, indapamide, clorexolone, and fenquizone.

In some embodiments, the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof. In some embodiments, the thiazide-like diuretic is quinethazone. In some embodiments, the thiazide-like diuretic is clopamide. In some embodiments, the thiazide-like diuretic is chlorthalidone. In some embodiments, the thiazide-like diuretic is mefruside. In some embodiments, the thiazide-like diuretic is clofenamide. In some embodiments, the thiazide-like diuretic is metolazone. In some embodiments, the thiazide-like diuretic is meticrane. In some embodiments, the thiazide-like diuretic is xipamide. In some embodiments, the thiazide-like diuretic is indapamide or the hydrate thereof. In some embodiments, the thiazide-like diuretic is indapamide. In some embodiments, the thiazide-like diuretic is clorexolone. In some embodiments, the thiazide-like diuretic is fenquizone.

Loop Diuretics

As used herein, loop diuretics are compounds that act on the Na+/K+/2Cl− cotransporter in the thick ascending loop of Henle to inhibit sodium, chloride and potassium reabsorption. Examples of loop diuretics include but are not limited to furosemide, bumetanide, etacrynic acid, etozolin, muzolimine, ozolinone, piretanide, tienilic acid, and torasemide. In some embodiments, the loop diuretic is furosemide, bumetanide, etacrynic acid, etozolin, muzolimine, ozolinone, piretanide, tienilic acid, torasemide, or a pharmaceutically acceptable salt or hydrate thereof.

Other Diuretics

Osmotic diuretics are compounds that cause water to be retained within the proximal tubule and descending limb of loop of Henle. In some embodiments, the osmotic diuretic expands fluid and plasma volume and increases blood flow to the kidney. Examples included but are not limited to mannitol and glycerol.

Carbonic Anhydrase Inhibitors

Carbonic anhydrase inhibitors as used herein are compounds that are inhibitors of carbonic anhydrase. In some embodiments, the carbonic anhydrase inhibitor increases the excretion of bicarbonate with accompanying sodium, potassium and water, which results in an increased flow of alkaline urine. In some embodiments, the carbonic anhydrase inhibitor inhibits the transport of bicarbonate into the interstitium from the proximal convoluted tubule, which leads to less sodium being reabsorbed and provides greater sodium, bicarbonate and water loss in the urine. Examples of such compounds include but are not limited to acetazolamide, dichlorphenamide, and methazolamide.

Potassium Sparing Diuretics

Potassium sparing diuretics are compounds that either compete with aldosterone for intracellular cytoplasmic receptor sites, or directly block sodium channels, specifically epithelial sodium channels (ENaC). Examples of potassium sparing diuretics include but are not limited to amiloride, spironolactone, eplerenone, triamterene, potassium canrenoate.

Other diuretics contemplated for use also include but are not limited to caffeine, theophylline, theobromine, tolvaptan, conivaptan, dopamine, caffeine, theophylline, theobromine, and pamabrom.

In some embodiments, the diuretic is dichlorphenamide, amiloride, pamabrom, mannitol, acetazolamide, methazolamide, spironolactone, triamterene, or the pharmaceutically acceptable salt or hydrate thereof. In some embodiments, the diuretic is dichlorphenamide. In some embodiments, the diuretic is amiloride. In some embodiments, the diuretic is pamabrom. In some embodiments, the diuretic is mannitol. In some embodiments, the diuretic is acetazolamide. In some embodiments, the diuretic is methazolamide. In some embodiments, the diuretic is spironolactone. In some embodiments, the diuretic is triamterene.

Calcium-Channel Blockers

As used herein, calcium-channel blockers are compounds that promote vasodilator activity by reducing calcium influx into vascular smooth muscle cells. In some embodiments, the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof. In some embodiments, the calcium-channel blocker is amlodipine, nifedipine, diltiazem, nimodipine, verapamil, isradipine, felodipine, nicardipine, nisoldipine, clevidipine or the pharmaceutically acceptable salt or hydrate thereof. In some embodiments, the calcium-channel blocker is amlodipine or the pharmaceutically acceptable salt thereof. In some embodiments, the calcium-channel blocker is amolodipine besylate. In some embodiments, the calcium-channel blocker is nifedipine. In some embodiments, the calcium-channel blocker is diltiazem. In some embodiments, the calcium-channel blocker is nimodipine. In some embodiments, the calcium-channel blocker is verapamil. In some embodiments, the calcium-channel blocker is isradipine. In some embodiments, the calcium-channel blocker is felodipine. In some embodiments, the calcium-channel blocker is nicardipine. In some embodiments, the calcium-channel blocker is nisoldipine. In some embodiments, the calcium-channel blocker is clevidipine.

Beta-Blockers

As used herein, beta-blockers are compounds that inhibit the receptor sites for the endogenous catecholamines epinephrine (adrenaline) and norepinephrine (noradrenaline) on adrenergic beta receptors, of the sympathetic nervous system. Synonyms include but are not limited to β-blockers, beta-adrenergic blocking agents, beta antagonists, beta-adrenergic antagonists, beta-adrenoreceptor antagonists, or beta adrenergic receptor antagonists. In some embodiments, beta-blockers inhibit activation of all types of β-adrenergic receptors. In some embodiments, beta-blockers inhibit both β-adrenergic receptors and α-adrenergic receptors. In some embodiments, beta-blockers are selective for one of following beta receptors: $\beta_1$, $\beta_2$ and $\beta_3$ receptors. In some embodiments, the beta-blocker is a non-selective beta-adrenoceptor antagonist. Examples of non-selective beta-adrenoceptor antagonists, include but are not limited, to pindolol, propranolol, oxprenolol, sotalol, timolol, carteolol, penbutolol, and nadolol. In some embodiments, the beta-blocker is a compound with combined β- and α-adrenoceptor blocking action. Suitable examples include but are not limited to carvedilol, bucindolol and labetolol. In some embodiments, the beta-blocker is a $\beta_1$-selective adrenoceptor antagonist Examples of $\beta_1$ selective adrenoceptor antagonist include but are not limited to atenolol, bisoprolol, betaxolol, metoprolol, celiprolol, esmolol, nebivolol, and acebutolol. In some embodiments, the beta blocker is $\beta_2$-selective adrenoceptor antagonist, such as butaxamine.

In some embodiments, the beta-blocker is acebutolol, atenolol, betaxolol, bisoprolol, carteolol, esmolol, penbutolol, metoprolol, nadolol, nebivolol, pindolol, sotalol, propranolol, carvedilol, labetalol, timolol, esmolol, celiprolol, oxprenolol, levobunolol, practolol, metipranolol, landiolol, bopindolol, pronethalol, butaxamine, bevantolol, tertatolol, arotinolol, levobetaxolol, befunolol, amosulalol, tilisolol, or the pharmaceutically acceptable salt or hydrate thereof. In some embodiments, the beta blocker is acebutolol, atenolol, betaxolol, bisoprolol, carteolol, esmolol, penbutolol, metoprolol, nadolol, nebivolol, pindolol, sotalol, propranolol, carvedilol, labetalol or the pharmaceutically acceptable salt or hydrate thereof. In some embodiments, the beta blocker is atenolol. In some embodiments, the beta blocker is bisoprolol or the pharmaceutically acceptable salt thereof. In some embodiments, the beta blocker is bisoprolol fumarate.

Lowest Hypertension Therapeutic Dose

As used herein, the lowest hypertension therapeutic dose (LHTD) refers to the lowest strength dose for the single agent for hypertension approved by the US Food and Drug Administration and is not marked as "discontinued" by the Orange Book database (http://www.accessdata.fda.gov/scripts/cder/ob/) as of the filing date of this application. The lowest hypertension therapeutic dose does not include the lowest manufactured dose for cases wherein the lowest hypertension therapeutic dose is not the same as the lowest manufactured dose. Furthermore, the lowest hypertension therapeutic dose does not include the dose as recommended by a physician for cases wherein the lowest hypertension therapeutic dose is not the same dose as recommended by a physician. Further, the lowest hypertension dose of the angiotensin II receptor blocker, diuretic, calcium channel blocker, or the beta-blocker described herein refers to the dose of the form of angiotensin II receptor blocker, diuretic, calcium channel blocker, or the beta-blocker approved for use by the US Food and Drug Administration, which includes the free base, pharmaceutically acceptable salt or hydrate thereof.

In some embodiments, the dose of the angiotensin II receptor blocker is from about 20% to about 60% of the lowest hypertension therapeutic dose. In some embodiments, the dose of the angiotensin II receptor blocker is from about 20% to about 50% of the lowest hypertension therapeutic dose. In some embodiments, the dose of the angiotensin II receptor blocker is from about 20% to about 40% of the lowest hypertension therapeutic dose. In some embodiments, the dose of the angiotensin II receptor blocker is from about 20% to about 30% of the lowest hypertension therapeutic dose. In some embodiments, the dose of the angiotensin II receptor is from about 30% to about 60% of the lowest hypertension therapeutic dose. In some embodiments, the dose of the angiotensin II receptor is from about 30% to about 50% of the lowest hypertension therapeutic dose. In some embodiments, the dose of the angiotensin II receptor blocker is from about 30% to about 40% of the lowest hypertension therapeutic dose. In some embodiments, the dose of the angiotensin II receptor blocker is from about 40% to about 60% of the lowest hypertension therapeutic dose. In some embodiments, the dose of the angiotensin II receptor blocker is from about 40% to about 50% of the lowest hypertension therapeutic dose. In some embodiments, the dose of the angiotensin II receptor blocker is from about 45% to about 55% of the lowest hypertension therapeutic dose. In some embodiments, the dose of the angiotensin II receptor blocker is from about 50% to about 60% of the lowest hypertension therapeutic dose.

In some embodiments, the dose of the angiotensin II receptor blocker is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin II receptor blocker is about 20%, about 21%, about 22%, about 23%, about 24%, about 25%, about 26%, about 27%, about 28%, about 29%, or about 30% of the lowest hypertension therapeutic dose. In some embodiments, the dose of the angiotensin II receptor blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin II receptor blocker is about 45%, about 46%, about 47%, about 48%, about 49%, about 50%, about 51%, about 52%, about 53%, about 54%, or about 55% of the lowest hypertension therapeutic dose. In some embodiments, the dose of the angiotensin II receptor blocker is about 25% of the lowest hypertension therapeutic dose. In some embodiments, the dose of the angiotensin II receptor blocker is about 50% of the lowest hypertension therapeutic dose.

In some embodiments, the dose of the diuretic is from about 20% to about 60% of the lowest hypertension therapeutic dose. In some embodiments, the dose of the diuretic is from about 20% to about 50% of the lowest hypertension therapeutic dose. In some embodiments, the dose of the diuretic is from about 20% to about 40% of the lowest hypertension therapeutic dose. In some embodiments, the dose of the diuretic is from about 20% to about 30% of the lowest hypertension therapeutic dose. In some embodiments, the dose of the diuretic is from about 30% to about 60% of the lowest hypertension therapeutic dose. In some embodiments, the dose of the diuretic is from about 30% to about 50% of the lowest hypertension therapeutic dose. In some embodiments, the dose of the diuretic is from about 30% to about 40% of the lowest hypertension therapeutic dose. In some embodiments, the dose of the diuretic is from about 40% to about 60% of the lowest hypertension therapeutic dose. In some embodiments, the dose of the diuretic is from about 40% to about 50% of the lowest hypertension therapeutic dose. In some embodiments, the dose of the diuretic is from about 45% to about 55% of the lowest hypertension therapeutic dose. In some embodiments, the dose of the diuretic is from about 50% to about 60% of the lowest hypertension therapeutic dose.

In some embodiments, the dose of the diuretic is about 20%/a, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the diuretic is about 20%, about 21%, about 22%, about 23%, about 24%, about 25%, about 26%, about 27%, about 28%, about 29%, or about 30% of the lowest hypertension therapeutic dose. In some embodiments, the dose of the diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the diuretic is about 45%, about 46%, about 47%, about 48%, about 49%, about 50%, about 51%, about 52%, about 53%, about 54%, or about 55% of the lowest hypertension therapeutic dose. In some embodiments, the dose of the diuretic is about 25% of the lowest hypertension therapeutic dose. In some embodiments, the dose of the diuretic is about 50% of the lowest hypertension therapeutic dose.

In some embodiments, the dose of the thiazide diuretic is from about 20% to about 60% of the lowest hypertension therapeutic dose. In some embodiments, the dose of the thiazide diuretic is from about 20% to about 50% of the lowest hypertension therapeutic dose. In some embodiments, the dose of the thiazide diuretic is from about 20% to about 40% of the lowest hypertension therapeutic dose. In some embodiments, the dose of the thiazide diuretic is from about 20% to about 30% of the lowest hypertension therapeutic dose. In some embodiments, the dose of the thiazide diuretic is from about 30% to about 60% of the lowest hypertension therapeutic dose. In some embodiments, the dose of the thiazide diuretic is from about 30% to about 50% of the lowest hypertension therapeutic dose. In some embodiments, the dose of the thiazide diuretic is from about 30% to about 40% of the lowest hypertension therapeutic dose. In some embodiments, the dose of the thiazide diuretic is from about 40% to about 60% of the lowest hypertension therapeutic dose. In some embodiments, the dose of the thiazide diuretic is from about 40% to about 50% of the lowest hypertension therapeutic dose. In some embodiments, the dose of the thiazide diuretic is from about 45% to about 55% of the lowest hypertension therapeutic dose. In some embodiments, the dose of the thiazide diuretic is from about 50% to about 60% of the lowest hypertension therapeutic dose.

In some embodiments, the dose of the thiazide diuretic is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide diuretic is about 20%, about 21%, about 22%, about 23%, about 24%, about 25%, about 26%, about 27%, about 28%, about 29%, or about 30% of the lowest hypertension therapeutic dose. In some embodiments, the dose of the thiazide diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide diuretic is about 45%, about 46%, about 47%, about 48%, about 49%, about 50%, about 51%, about 52%, about 53%, about 54%, or about 55% of the lowest hypertension therapeutic dose. In some embodiments, the dose of the thiazide diuretic is about 25% of the lowest hypertension therapeutic dose. In some embodiments, the dose of the thiazide diuretic is about 50% of the lowest hypertension therapeutic dose.

In some embodiments, the dose of the thiazide-like diuretic is from about 20% to about 60% of the lowest hypertension therapeutic dose. In some embodiments, the dose of the thiazide-like diuretic is from about 20% to about 50% of the lowest hypertension therapeutic dose. In some embodiments, the dose of the thiazide-like diuretic is from about 20% to about 40% of the lowest hypertension therapeutic dose. In some embodiments, the dose of the thiazide-like diuretic is from about 20% to about 30% of the lowest hypertension therapeutic dose. In some embodiments, the dose of the thiazide-like diuretic is from about 30% to about 60% of the lowest hypertension therapeutic dose. In some embodiments, the dose of the thiazide-like diuretic is from about 30% to about 50% of the lowest hypertension therapeutic dose. In some embodiments, the dose of the thiazide-like diuretic is from about 30% to about 40% of the lowest hypertension therapeutic dose.

In some embodiments, the dose of the thiazide diuretic is from about 40% to about 60% of the lowest hypertension therapeutic dose. In some embodiments, the dose of the thiazide-like diuretic is from about 40% to about 50% of the lowest hypertension therapeutic dose. In some embodiments, the dose of the thiazide-like diuretic is from about 45% to about 55% of the lowest hypertension therapeutic dose. In some embodiments, the dose of the thiazide-like diuretic is from about 50% to about 60% of the lowest hypertension therapeutic dose.

In some embodiments, the dose of the thiazide-like diuretic is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide-like diuretic is about 20%, about 21%, about 22%, about 23%, about 24%, about 25%, about 26%, about 27%, about 28%, about 29%, or about 30% of the lowest hypertension therapeutic dose. In some embodiments, the dose of the thiazide-like diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide-like diuretic is about 45%, about 46%, about 47%, about 48%, about 49%, about 50%, about 51%, about 52%, about 53%, about 54%, or about 55% of the lowest hypertension therapeutic dose. In some embodiments, the dose of the thiazide-like diuretic is about 25% of the lowest hypertension therapeutic dose. In some embodiments, the dose of the thiazide-like diuretic is about 50% of the lowest hypertension therapeutic dose.

In some embodiments, the dose of the loop diuretic is from about 20% to about 60% of the lowest hypertension therapeutic dose. In some embodiments, the dose of the loop diuretic is from about 20% to about 50% of the lowest hypertension therapeutic dose. In some embodiments, the dose of the loop diuretic is from about 20% to about 40% of the lowest hypertension therapeutic dose. In some embodiments, the dose of the loop diuretic is from about 20% to about 30% of the lowest hypertension therapeutic dose. In some embodiments, the dose of the loop diuretic is from about 30% to about 60% of the lowest hypertension therapeutic dose. In some embodiments, the dose of the loop diuretic is from about 30% to about 50% of the lowest hypertension therapeutic dose. In some embodiments, the dose of the loop diuretic is from about 30% to about 40% of the lowest hypertension therapeutic dose. In some embodiments, the dose of the loop is from about 40% to about 60% of the lowest hypertension therapeutic dose. In some embodiments, the dose of the loop diuretic is from about 40% to about 50% of the lowest hypertension therapeutic dose. In some embodiments, the dose of the loop diuretic is from about 45% to about 55% of the lowest hypertension therapeutic dose. In some embodiments, the dose of the loop diuretic is from about 50% to about 60% of the lowest hypertension therapeutic dose.

In some embodiments, the dose of the loop diuretic is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the loop diuretic is about 20%, about 21%, about 22%, about 23%, about 24%, about 25%, about 26%, about 27%, about 28%, about 29%, or about 30% of the lowest hypertension therapeutic dose. In some embodiments, the dose of the loop diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the loop diuretic is about 45%, about 46%, about 47%, about 48%, about 49%, about 50%, about 51%, about 52%, about 53%, about 54%, or about 55% of the lowest hypertension therapeutic dose. In some embodiments, the dose of the loop diuretic is about 25% of the lowest hypertension therapeutic dose. In some embodiments, the dose of the loop diuretic is about 50% of the lowest hypertension therapeutic dose.

In some embodiments, the dose of the calcium channel blocker is from about 20% to about 60% of the lowest hypertension therapeutic dose. In some embodiments, the dose of the calcium channel blocker is from about 20% to about 50% of the lowest hypertension therapeutic dose. In some embodiments, the dose of the calcium channel blocker is from about 20% to about 40% of the lowest hypertension therapeutic dose. In some embodiments, the dose of the calcium channel blocker is from about 20% to about 30% of the lowest hypertension therapeutic dose. In some embodiments, the dose of the calcium channel blocker is from about 30% to about 60% of the lowest hypertension therapeutic dose. In some embodiments, the dose of the calcium channel blocker is from about 30% to about 50% of the lowest hypertension therapeutic dose. In some embodiments, the dose of the calcium channel blocker is from about 30% to about 40% of the lowest hypertension therapeutic dose. In some embodiments, the dose of the calcium channel blocker is from about 40% to about 60% of the lowest hypertension therapeutic dose. In some embodiments, the dose of the calcium channel blocker is from about 40% to about 50% of the lowest hypertension therapeutic dose. In some embodiments, the dose of the calcium channel blocker is from about 45% to about 55% of the lowest hypertension therapeutic dose. In some embodiments, the dose of the calcium channel blocker is from about 50% to about 60% of the lowest hypertension therapeutic dose.

In some embodiments, the dose of the calcium channel blocker is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the calcium channel blocker is about 20%, about 21%, about 22%, about 23%, about 24%, about 25%, about 26%, about 27%, about 28%, about 29%, or about 30% of the lowest hypertension therapeutic dose. In some embodiments, the dose of the calcium channel blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the calcium channel blocker is about 45%, about 46%, about 47%, about 48%, about 49%, about 50%/a, about 51%, about 52%, about 53%, about 54%, or about 55% of the lowest hypertension therapeutic dose. In some embodiments, the dose of the calcium channel blocker is about 25% of the lowest hypertension therapeutic dose. In some embodiments, the dose of the calcium channel blocker is about 50% of the lowest hypertension therapeutic dose.

In some embodiments, the dose of the beta-blocker is from about 20% to about 60% of the lowest hypertension therapeutic dose. In some embodiments, the dose of the beta-blocker is from about 20% to about 50% of the lowest hypertension therapeutic dose. In some embodiments, the dose of the beta-blocker is from about 20% to about 40% of the lowest hypertension therapeutic dose. In some embodiments, the dose of the beta-blocker is from about 20% to about 30% of the lowest hypertension therapeutic dose. In some embodiments, the dose of the beta-blocker is from about 30% to about 60% of the lowest hypertension therapeutic dose. In some embodiments, the dose of the beta-blocker is from about 30% to about 50% of the lowest hypertension therapeutic dose. In some embodiments, the dose of the beta-blocker is from about 30% to about 40% of the lowest hypertension therapeutic dose. In some embodiments, the dose of the beta-blocker is from about 40% to about 60% of the lowest hypertension therapeutic dose. In some embodiments, the dose of the beta-blocker is from about 40% to about 50% of the lowest hypertension therapeutic dose. In some embodiments, the dose of the beta-blocker is from about 45% to about 55% of the lowest hypertension therapeutic dose. In some embodiments, the dose of the beta-blocker is from about 50% to about 60% of the lowest hypertension therapeutic dose.

In some embodiments, the dose of the beta-blocker is about 20%/a, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the beta-blocker is about 20%, about 21%, about 22%, about 23%, about 24%, about 25%, about 26%, about 27%, about 28%, about 29%, or about 30% of the lowest hypertension therapeutic dose. In some embodiments, the dose of the beta-blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the beta-blocker is about 45%, about 46%, about 47%, about 48%, about 49%, about 50%, about 51%, about 52%, about 53%, about 54%, or about 55% of the lowest hypertension therapeutic dose. In some embodiments, the dose of the beta-blocker is about 25% of the lowest hypertension therapeutic dose. In some embodiments, the dose of the beta-blocker is about 50% of the lowest hypertension therapeutic dose.

In some embodiments, the lowest hypertension therapeutic dose (LHTD) and the corresponding proposed dose and proposed dose range for the following compounds are as described in the following table:

| Agent | Lowest Hypertension Therapeutic Dose (mg) | Proposed Dose (mg) | Proposed Dose Range (mg) |
|---|---|---|---|
| Amlodipine besylate | 2.5 | 1.25 | 1-1.5 |
| Atenolol | 25 | 12.5 | 10-15 |
| Bisoprolol Fumarate | 5 | 2.5 | 2-3 |
| Chlorthalidone | 25 | 12.5 | 10-15 |
| Hydrochlorothiazide | 12.5 | 6.25 | 5-7.5 |
| Indapamide | 1.25 | 0.625 | 0.5-0.75 |
| Irbesartan | 75 | 37.5 | 30-45 |
| Telmisartan | 20 | 10 | 8-12 |

In some embodiments, the pharmaceutical composition comprises: (a) irbesartan as an angiotensin II receptor blocker; (b) hydrochlorothiazide as a thiazide diuretic; (c) amlodipine besylate as a calcium channel blocker; and (d) atenolol as a beta-blocker. In some embodiments, the dose of irbesartan is about 30 mg to about 45 mg, the dose of hydrochlorothiazide is about 5 mg to about 7.5 mg, the dose of amlodipine besylate is about 1 mg to about 1.5 mg, and the dose of atenolol is about 10 mg to about 15 mg. In some embodiments, the dose of irbesartan is about 37.5 mg, the dose of hydrochlorothiazide is about 6.25 mg, the dose of amlodipine besylate is about 1.25 mg, and the dose of atenolol is about 12.5 mg.

In some embodiments, the pharmaceutical composition comprises: (a) telmisartan as an angiotensin II receptor blocker; (b) hydrochlorothiazide as a thiazide diuretic; (c) amlodipine besylate as a calcium channel blocker; and (d) atenolol as a beta-blocker. In some embodiments, the dose of telmisartan is about 8 mg to about 12 mg, the dose of hydrochlorothiazide is about 5 mg to about 7.5 mg, the dose of amlodipine besylate is about 1 mg to about 1.5 mg, and the dose of atenolol is about 10 mg to about 15 mg. In some embodiments, the dose of telmisartan is about 10 mg, the dose of hydrochlorothiazide is about 6.25 mg, the dose of amlodipine besylate is about 1.25 mg, and the dose of atenolol is about 12.5 mg.

In some embodiments, the pharmaceutical composition comprises: (a) irbesartan as an angiotensin II receptor blocker; (b) indapamide as a thiazide-like diuretic; (c) amlodipine besylate as a calcium channel blocker; and (d) bisoprolol fumarate as a beta-blocker. In some embodiments, the dose of irbesartan is about 30 mg to about 45 mg, the dose of indapamide is about 0.5 mg to about 0.75 mg, the dose of amlodipine besylate is about 1 mg to about 1.5 mg, and the dose of bisoprolol fumarate is about 2 mg to about 3 mg. In some embodiments, the dose of irbesartan is about 37.5 mg, the dose of indapamide is about 0.625 mg, the dose of amlodipine besylate is about 1.25 mg, and the dose of bisoprolol fumarate is about 2.5 mg.

In some embodiments, the pharmaceutical composition comprises: (a) telmisartan as an angiotensin II receptor blocker; (b) indapamide as a thiazide-like diuretic; (c) amlodipine besylate as a calcium channel blocker; and (d) bisoprolol fumarate as a beta-blocker. In some embodiments, the dose of telmisartan is about 8 mg to about 12 mg, the dose of indapamide is about 0.5 mg to about 0.75 mg, the dose of amlodipine besylate is about 1 mg to about 1.5 mg, and the dose of bisoprolol fumarate is about 2 mg to about 3 mg. In some embodiments, dose of telmisartan is about 10 mg, the dose of indapamide is about 0.625 mg, the dose of amlodipine besylate is about 1.25 mg, and the dose of bisoprolol fumarate is about 2.5 mg.

In some embodiments, the pharmaceutical composition comprises: (a) telmisartan as an angiotensin II receptor blocker; (b) chlorthalidone as a thiazide-like diuretic; (c) amlodipine besylate as a calcium channel blocker; and (d) bisoprolol fumarate as a beta-blocker. In some embodiments, the dose of telmisartan is about 8 mg to about 12 mg, the dose of chlorthalidone is about 10 mg to about 15 mg the dose of amlodipine besylate is about 1 mg to about 1.5 mg, and the dose of bisoprolol fumarate is about 2 mg to about 3 mg. In some embodiments, dose of telmisartan is about 10 mg, the dose of chlorthalidone is about 12.5 mg, the dose of amlodipine besylate is about 1.25 mg, and the dose of bisoprolol fumarate is about 2.5 mg.

In some embodiments, the pharmaceutical composition comprises: (a) telmisartan as an angiotensin II receptor blocker; (b) chlorthalidone as a thiazide-like diuretic; (c) amlodipine besylate as a calcium channel blocker; and (d) atenolol as a beta-blocker. In some embodiments, the dose of telmisartan is about 8 mg to about 12 mg, the dose of chlorthalidone is about 10 mg to about 15 mg, the dose of amlodipine besylate is about 1 mg to about 1.5 mg, and the dose of atenolol is about 10 mg to about 15 mg. In some embodiments, the dose of telmisartan is about 10 mg, the dose of chlorthalidone is about 12.5 mg, the dose of amlodipine besylate is about 1.25 mg, and the dose of atenolol is about 12.5 mg.

In some embodiments, the pharmaceutical composition comprises: (a) irbesartan as an angiotensin II receptor blocker; (b) chlorthalidone as a thiazide-like diuretic; (c) amlodipine besylate as a calcium channel blocker; and (d) bisoprolol fumarate as a beta-blocker. In some embodiments, the dose of irbesartan is about 30 mg to about 45 mg, the dose of chlorthalidone is about 10 mg to about 15 mg, the dose of amlodipine besylate is about 1 mg to about 1.5 mg, and the dose of bisoprolol fumarate is about 2 mg to about 3 mg. In some embodiments, dose of irbesartan is about 37.5 mg, the dose of chlorthalidone is about 12.5 mg, the dose of amlodipine besylate is about 1.25 mg, and the dose of bisoprolol fumarate is about 2.5 mg.

In some embodiments, the pharmaceutical composition comprises: (a) irbesartan as an angiotensin II receptor blocker; (b) chlorthalidone as a thiazide-like diuretic; (c) amlodipine besylate as a calcium channel blocker; and (d) atenolol as a beta-blocker. In some embodiments, the dose of irbesartan is about 30 mg to about 45 mg, the dose of chlorthalidone is about 10 mg to about 15 mg, the dose of amlodipine besylate is about 1 mg to about 1.5 mg, and the dose of atenolol is about 10 mg to about 15 mg. In some embodiments, the dose of irbesartan is about 37.5 mg, the dose of chlorthalidone is about 12.5 mg, the dose of amlodipine besylate is about 1.25 mg, and the dose of atenolol is about 12.5 mg.

Formulations

In some embodiments, the angiotensin II receptor blocker, the diuretic, the calcium channel blocker and the beta-blocker are provided in one formulation. In some embodiments, the angiotensin II receptor blocker, the diuretic, the calcium channel blocker and the beta-blocker are each provided in a separate formulation. In some embodiments, two of the angiotensin II receptor blocker, the diuretic, the calcium channel blocker and the beta-blocker are provided in one formulation. In some embodiments, the angiotensin II receptor and the diuretic are provided in one formulation. In some embodiments, the angiotensin II receptor blocker and the calcium channel blocker are provided in one formulation. In some embodiments, the angiotensin II receptor blocker and the beta-blocker are provided in one formulation. In some embodiments, the diuretic and the calcium channel blocker are provided in one formulation. In some embodiments, the diuretic and the beta-blocker are provided in one formulation. In some embodiments, the calcium channel blocker and the beta-blocker are provided in one formulation. In some embodiments, three of the angiotensin II receptor blocker, the diuretic, the calcium channel blocker and the beta-blocker are provided in one formulation. In some embodiments, the angiotensin II receptor blocker, the diuretic and the calcium channel blocker are provided in one formulation. In some embodiments, the diuretic, the calcium channel blocker and the beta-blocker are provided in one formulation. In some embodiments, the pharmaceutical composition is in the form of pill, tablet or capsule. In some embodiments, the pharmaceutical composition is in the form of pill. In some embodiments, the pharmaceutical composition is in the form of tablet. In some embodiments, the pharmaceutical composition is in the form of capsule. In some embodiments, the pharmaceutical composition is suitable for oral administration.

Other suitable formulations include but are not limited to those suitable for rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose.

Exemplary pharmaceutical compositions may be used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. In some embodiments, capsules are prepared by encapsulating tablets in hard-gelatin capsules (e.g. overencapsulation.) Tablets, and other solid dosage forms, such as dragees, capsules, pills and granules, may optionally be scored or prepared with coatings and shells, such as enteric coatings and other coatings well known in the pharmaceutical-formulating art.

In some embodiments, the angiotensin II receptor blockers of the pharmaceutical compositions described herein can be replaced with angiotensin converting enzyme inhibitors (ACE inhibitors). Examples of suitable angiotensin converting enzyme inhibitors include but are not limited to benazepril, captopril, enalapril, fosinopril, lisinopril, moexipril, perindopril, quinapril, ramipril, trandolapril or the pharmaceutically acceptable salt or hydrate thereof. In some embodiments, the dose of the angiotensin converting enzyme inhibitor is from about 20% to about 60% of the lowest hypertension therapeutic dose. In some embodiments, the dose of the angiotensin converting enzyme inhibitor is from about 40% to about 60% of the lowest hypertension therapeutic dose. In some embodiments, the dose of the angiotensin converting enzyme inhibitor is from about 45% to about 55% of the lowest hypertension therapeutic dose. In some embodiments, the dose of the angiotensin converting enzyme inhibitor is about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin converting enzyme inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin converting enzyme inhibitor is about 45%, about 46%, about 47%, about 48%, about 49%, about 50%, about 51%, about 52%, about 53%, about 54%, or about 55% of the lowest hypertension therapeutic dose. In some embodiments, the dose of the angiotensin converting enzyme inhibitor is about 50% of the lowest hypertension therapeutic dose.

Methods of Treatment

The pharmaceutical compositions described herein are useful for treating hypertension in a subject in need thereof. In some embodiments, the treatment results in a systolic blood pressure (SBP) of less than about 140 mmHg. In some embodiments, the treatment results in a systolic blood pressure (SBP) of less than about 135 mmHg. In some embodiments, the treatment results in a reduction of systolic blood pressure (SBP) of about 10 mmHg or greater. In some embodiments, the treatment results in a reduction of systolic blood pressure (SBP) of about 10 mmHg to about 20 mmHg. In some embodiments, the treatment results in a reduction of systolic blood pressure (SBP) of about 10 mmHg to about 30 mmHg. In some embodiments, the treatment results in a reduction of systolic blood pressure (SBP) of about 10 mmHg, about 11 mmHg, about 12 mmHg, about 13 mmHg about 14 mmHg about 15 mmHg about 16 mmHg about 17 mmHg about 18 mmHg about 19 mmHg, or about 20 mmHg. In some embodiments, the treatment results in a reduction of systolic blood pressure (SBP) of about 10 mmHg, about 11 mmHg, about 12 mmHg, about 13 mmHg, about 14 mmHg, about 15 mmHg, about 16 mmHg, about 17 mmHg about 18 mmHg about 19 mmHg about 20 mmHg about 21 mmHg about 22 mmHg, about 23 mmHg, about 24 mmHg, about 25 mmHg about 26 mmHg about 27 mmHg about 28 mmHg about 29 mmHg or about 30 mmHg. In some embodiments, the treatment results in a diastolic blood pressure (DBP) of less than about 90 mmHg. In some embodiments, the treatment results in a diastolic blood pressure (DBP) of less than about 85 mmHg. In some embodiments, treatment results in a reduction of diastolic blood pressure (DBP) of about 5 mmHg or greater. In some embodiments, treatment results in a reduction of diastolic blood pressure (DBP) of about 5 mmHg to about 10 mmHg. In some embodiments, treatment results in a reduction of diastolic blood pressure (DBP) of about 5 mmHg to about 15 mmHg. In some embodiments, treatment results in a reduction of diastolic blood pressure (DBP) of about 5 mmHg about 6 mmHg about 7 mmHg, about 8 mmHg, about 9 mmHg, or about 10 mmHg. In some embodiments, treatment results in a reduction of diastolic blood pressure (DBP) of about 5 mmHg about 6 mmHg about 7 mmHg about 8 mmHg about 9 mmHg about 10 mmHg about 11 mmHg about 12 mmHg about 13 mmHg about 14 mmHg or about 15 mmHg.

In some embodiments, treatment results in a reduction in systolic blood pressure (SBP) that is greater than the reduction obtained with the full lowest hypertension therapeutic dose of any one of the angiotensin II receptor blocker, the diuretic, the calcium channel blocker and the beta-blocker in the pharmaceutical composition. In some embodiments, treatment results in a reduction in systolic blood pressure (SBP) that is greater than the reduction obtained with the full lowest hypertension therapeutic dose of the angiotensin II receptor blocker in the pharmaceutical composition. In some embodiments, treatment results in a reduction in systolic blood pressure (SBP) that is greater than the reduction obtained with the full lowest hypertension therapeutic dose of the diuretic in the pharmaceutical composition. In some embodiments, treatment results in a reduction in systolic blood pressure (SBP) that is greater than the reduction obtained with the full lowest hypertension therapeutic dose of the calcium channel blocker in the pharmaceutical composition. In some embodiments, treatment results in a reduction in systolic blood pressure (SBP) that is greater than the reduction obtained with the full lowest hypertension therapeutic dose of the beta-blocker in the pharmaceutical composition.

In some embodiments, treatment results in a reduction in diastolic blood pressure (DBP) that is greater than the reduction obtained with the full lowest hypertension therapeutic dose of any one of the angiotensin II receptor blocker, the diuretic, the calcium channel blocker and the beta-blocker in the pharmaceutical composition. In some embodiments, treatment results in a reduction in diastolic blood pressure (DBP) that is greater than the reduction obtained with the full lowest hypertension therapeutic dose of the angiotensin II receptor blocker in the pharmaceutical composition. In some embodiments, treatment results in a reduction in diastolic blood pressure (DBP) that is greater than the reduction obtained with the full lowest hypertension therapeutic dose of the diuretic in the pharmaceutical composition. In some embodiments, treatment results in a reduction in diastolic blood pressure (DBP) that is greater than the reduction obtained with the full lowest hypertension therapeutic dose of the calcium channel blocker in the pharmaceutical composition. In some embodiments, treatment results in a reduction in diastolic blood pressure (DBP) that is greater than the reduction obtained with the full lowest hypertension therapeutic dose of the beta-blocker in the pharmaceutical composition.

In some embodiments, treatment results in greater long term tolerability and reduced risk of side effects when compared to treatment with the full lowest hypertension therapeutic dose of any one of the angiotensin II receptor blocker, the diuretic, the calcium channel blocker and the beta-blocker in the pharmaceutical composition. In some embodiments, the treatment results in greater long term tolerability and reduced risk of side effects when compared to treatment with the full lowest hypertension therapeutic dose of the angiotensin II receptor blocker in the pharmaceutical composition. In some embodiments, the treatment results in greater long term tolerability and reduced risk of side effects when compared to treatment with the full lowest hypertension therapeutic dose of the diuretic in the pharmaceutical composition. In some embodiments, the treatment results in greater long term tolerability and reduced risk of side effects when compared to treatment with the full lowest hypertension therapeutic dose of the calcium channel blocker in the pharmaceutical composition. In some embodiments, the treatment results in greater long term tolerability and reduced risk of side effects when compared to treatment with the full lowest hypertension therapeutic dose of the beta-blocker in the pharmaceutical composition.

In some embodiments, treatment results in a reduction in systolic blood pressure (SBP) that is greater than or equal to the reduction obtained with the combination of any two of the angiotensin II receptor blocker, the diuretic, the calcium channel blocker and the beta-blocker in the pharmaceutical composition, wherein the dose of each angiotensin II receptor blocker, the diuretic, the calcium channel blocker and the beta-blocker is about 50% of the lowest hypertension therapeutic dose. In some embodiments, treatment results in a reduction in diastolic blood pressure (DBP) that is greater than or equal to the reduction obtained with a combination of any two of the angiotensin II receptor blocker, the diuretic, the calcium channel blocker and the beta-blocker in the pharmaceutical composition, wherein the dose of each the angiotensin II receptor blocker, the diuretic, the calcium channel blocker and the beta-blocker is about 50% of the lowest hypertension therapeutic dose. In some embodiments, the treatment results in greater long term tolerability and reduced risk of side effects when compared to treatment with a combination of any two of (the angiotensin II receptor blocker, the diuretic, the calcium channel blocker and the beta-blocker in the pharmaceutical composition, wherein the dose of each the angiotensin II receptor blocker, the diuretic, the calcium channel blocker and the beta-blocker is about 50% of the lowest hypertension therapeutic dose.

In some embodiments, the treatment is the initial or first-line treatment of hypertension. In some embodiments, the subject has a very mild elevation of blood pressure prior to treatment. In some embodiments, the subject is not on any previous hypertension therapy prior to treatment. In some embodiments, the subject has a very mild elevation of blood pressure prior to treatment and is not on any previous hypertension therapy prior to treatment.

This present disclosure recognizes that the use of the angiogensin II receptor blocker in the pharmaceutical compositions disclosed herein in some embodiments provides beneficial therapeutic effects, which include but are not limited to significant reduction in blood pressure, significant reduction in blood pressure among subjects with mild elevation in blood pressure, greater long term tolerability, and reduced risk of side effects. This present disclosure recognizes that the exclusion of a lipid-regulating agent, a platelet function altering agent, a serum homocysteine lowering agent, or a combination thereof in the pharmaceutical compositions disclosed herein in some embodiments provides beneficial therapeutic effects, which include but are not limited to significant reduction in blood pressure, significant reduction in blood pressure among subjects with mild elevation in blood pressure, greater long term tolerability, and reduced risk of side effects.

EXAMPLES

Example 1: Quadruple Combination Composition Therapy (Quadpill) for the Treatment of Hypertension Methods The Quadpill study was a randomized, placebo-controlled, double-blind cross-over trial. The study was divided into three phases (FIG. 1). During the first phase (4 weeks) participants were randomized (1:1) to either receive Quadpill or Placebo. This was followed by a two week washout (placebo) and subsequently participants were crossed over to the opposite arm to receive the other treatment for four weeks (FIG. 1). Participants were recruited from the community, predominantly through community general practices in western Sydney, Australia.

Participants

Participants were eligible if they met the following inclusion criteria: 1) adults aged 18 years and over, 2) office SBP>140 mmHg and/or DBP>90 mmHg on 2 readings on separate days; plus baseline ambulatory SBP>135 and/or DBP>85; 3) Not on medical treatment for hypertension. Exclusion criteria included: No definite contraindication to one or more component medications in the Quadpill; the responsible clinician felt a change in current therapy would place the patient at risk; severe or accelerated hypertension; pregnancy; inability to provide informed consent; and medical illness with anticipated life expectancy less than 3 months.

Intervention

The Quadpill was a single encapsulated pill containing the four following components in the specified amounts: irbesartan (37.5 mg), amlodipine beyslate (1.25 mg), hydrochlorothiazide (6.25 mg) and atenolol (12.5 mg). The placebo capsule appeared identical and contained four placebo tablets of similar weight to those in the Quadpill.

Participants were administered a single pill, Quadpill or placebo, throughout the trial. Patients were instructed to take the tablets at the same time each day and encouraged to take this in the morning, but the time of the day (morning or evening) was at the patient's preference.

All trial medicines were prepared by a TGA-cGMP (Therapeutic Goods Australia—certificate of Good Manufacturing Practice) licensed manufacturing facility. Low strength doses were obtained by halving half-strength doses using a pill splitting device, without crushing, and were weighed to ensure accuracy of halving doses. The low strength doses were than encapsulated using gelatin capsules (DBCaps-Capsugel). The capsules were stored in a cool dry place and monitored using temperature loggers, until they were dispensed.

Treatment allocations were blinded to both study staff and participants. In addition to the study drugs, all participants were offered education on healthier lifestyle options as recommended by guidelines for hypertension management.

Randomization

A computer assisted randomization sequence was generated by a statistician and supplied to the pharmaceutical packaging company. The research assistant, recruitment team, investigators were blinded to this sequence. For each patient i.e. allocated randomization number, the pills were packaged into three child-resistant packs corresponding to three phases of the study. All packs had identical appearance ensuring blinding of patient and research staff. Subsequently the medication packs were prescribed in an organized sequence.

Outcomes and Data Collection

The primary outcome was reduction in mean 24 hour systolic blood pressure at 4 weeks using ambulatory blood pressure monitoring (ABP). The secondary outcomes included:
 a. Reduction in mean 24 hour diastolic blood pressure, and in daytime and nighttime SBP and DBP at 4 weeks
 b. Reduction in office SBP and DBP as measured by a standardized automated blood pressure cuff
 c. Proportion with controlled blood pressure at 4 weeks, defined as <135/85 mmHg 24 hour BP and <140/90 mmHg office BP
 d. Adverse events and pre-specified adverse events by laboratory parameters: Rise in transaminases (ALT/AST) more than 3× upper limit of normal or doubling if baseline levels known to be elevated; drop in estimated glomerular filtration rate by >20% as estimated from serum creatinine; sodium, potassium and uric acid levels
 e. Assessment of acceptability and tolerability Patients underwent 24 hour ABP monitoring 4 times— baseline (off study drug), 4 weeks (on phase 1 drug), 6 weeks (on placebo) and 10 weeks (on phase 3 drug). In order to minimize inconvenience, patients were referred for ABP to a lab. The ABP units were calibrated at regular intervals by the lab according to the manufacturer's specification. To minimize variability, the follow up readings were repeated from the same collection center using the same brand device. Participants were reimbursed nominal amounts to cover travel and parking costs. Study medications and investigations were provided at no cost to participants. Office BP was recorded three times at each visit using an OMRON T9P (HEM-759-C1). The second and the third readings were averaged for study analysis. In addition at week 4 and 10 patients underwent blood tests to assess for biochemical side effects, were administered a questionnaire for clinical side effects, and compliance was assessed by self-report and pill count. Patients remained blinded to their treatment allocation when completing this questionnaire.

Drug acceptability and tolerability were also assessed at the end of the study. All adverse events were recorded. In addition, clinical adverse events possibly associated with blood pressure lowering medications: dizziness, blurred vision, syncope/collapse, chest pain/angina, shortness of breath, cough, wheeze, pedal oedema, skin rash, itching were specifically asked about.

The trial had a simplified data safety and management committee of two core members with expertise in clinical medicine, trials and statistics. A single meeting was convened when 10 patients were randomized to the trial to review safety, and the study was advised to continue.

Statistical Considerations

A sample size of 50 patients was planned to provide 90% power at p=0.05 to detect a SBP difference of 12 mmHg between the intervention and control assuming a SD of the within patient difference of 12 mmHg, taking into account the possibility of a 10% loss to follow-up. The study ended at one year at the end of the budget and staffing time allocated and the original sample size was not reached.

Statistical Approach

Analyses were conducted on an intention to treat basis. All tests were two-sided and the nominal level of a was 5%. All statistical analyses were unadjusted for prognostic covariates. We reported compliance to the study drug using data on pills (doses) taken and missed doses over the time period.

A linear mixed model was used to estimate the effect of the treatment on change in blood pressure from baseline for each treatment period, according to the Kenward and Roger approach (Kenward M G, Roger J H. The use of baseline covariates in crossover studies. *Biostatistics* 2010; 11(1): 1-17.) In order to appropriately adjust for baseline levels, collected at the beginning of each treatment period (week 0, week 6), this method uses all measurements (baseline and follow-up, in both period) as outcomes, but accounts for covariance between measurements within individuals (Liu G F, Lu K, Mogg R, Mallick M, Mehrotra D V. Should baseline be a covariate or dependent variable in analyses of change from baseline in clinical trials? Stat Med 2009; 28(20): 2509-30). A linear contrast between the variables denoting period (first/second), type of measurement (baseline/final), and treatment received (placebo/Quadpill) produces an unbiased estimate of effect of the Quadpill on change in blood pressure compared to the placebo. All available data were included in the model, no missing data was imputed. If a patient had missing data for one period, data from the available period were used. A sensitivity analysis was carried including only patients with data available from both periods to see if the effect of treatment is modified. There was also adjustment of the denominator degrees of freedom of Kenward and Roger (2009) that is optimal for smaller sample sizes (Kenward M G, Roger J H. An improved approximation to the precision of fixed effects from restricted maximum likelihood. Computational Statistics & Data Analysis 2009; 53(7): 2583-95).

Testing for carry over used an unpaired t-test of the main outcome with order as an effect. Period effect was tested by using a paired t-test comparing the main outcome in period 1 with main outcome in period 2 from the same patient. A sensitivity analysis was aso performed using normal paired t-test to compare primary outcome between different period (different treatment) from the same patient, ignoring the baseline level of each period.

Continuous secondary endpoints with baseline values (e.g. daytime/night-time ambulatory SBP/DBP) were analyzed similarly to the primary endpoint. Other continuous variables without a baseline value in each period were analyzed with a paired t-test. Counts and percentages of all adverse events were reported. As a sensitivity analysis, the analyses were repeated on the 18 complete-cases (i.e. full data for each measurement period) data and showed similar findings to those reported here.

Tests for interaction of treatment effect with age ($\leq 60$ vs. $>60$ years), gender, and BMI ($\leq 30$ vs. $<30$ kg/m$^2$). Subgroup analyses for each variable were also conducted. All analyses were conducted using SAS 9.4 (Cary, N.C., USA) on software.

Results

Figure 2:
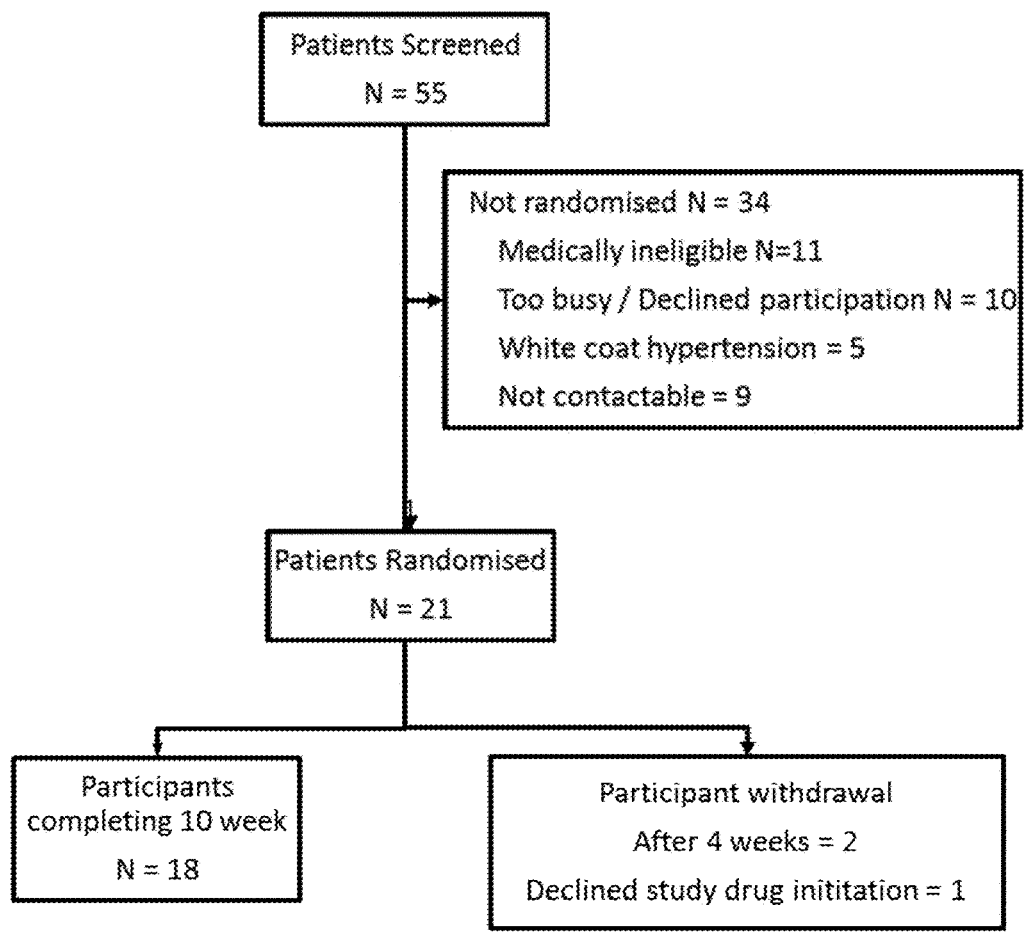
FIG. 2 shows the study flow diagram of Example 1.

Of 55 patients screened, 21 participants were eligible, one patient declined prior to drug initiation. Twenty were randomised between November 2014 and December 2015 and two withdrew at the end of the first treatment period because of social reasons (FIG. 2) Baseline characteristics of the study population are shown in Table 1.

TABLE 1

Baseline characteristics

| Characteristics | |
|---|---|
| Mean age, years (SD) | 57.7 (11.2) |
| 24 hour SBP/DBP (mmHg) | 140.1 (19.1)/87.0 (8.3) |
| Office BP (mmHg) | 154.1 (14.1)/90.3 (11.4) |
| Mean months since diagnosis of hypertension (SD) | 4.2 (5.4) |
| Female | 11 (52%) |
| University education | 9 (43%) |
| Diabetes | 2 (10%) |
| Hyperlipidemia | 5 (24%) |
| Previous myocardial infarction | 0 (0%) |

TABLE 1-continued

Baseline characteristics

| Characteristics | |
|---|---|
| Coronary artery revascularization | 0 (0%) |
| Cerebrovascular disease | 0 (0%) |
| Previous depression | 4 (19%) |
| Current smoker | 5 (45.5%) |

The difference in mean 24-hour SBP between Quadpill and placebo periods was −18.7 mmHg, 95% CI −23.0; −14.3. (Table 2) The placebo-corrected reduction in mean 24 hour SBP/DBP was 22/15 mmHg during the day time and 10/12 mmHg overnight. Office SBP was reduced by 22.4 mmHg, 95% CI 16.5-28.3 and DBP by 13.1 mmHg, 95% CI 8.8-17.3. Overall 15/18 (83%) participants achieved a mean ambulatory SBP <135 and DBP <85 mmHg when taking the Quadpill, compared to 7/18 (39%) when taking placebo (p=0.0053). All participants achieved an office SBP <140 and DBP<90 mmHg on the Quadpill compared to 6/18 (33%) on placebo (p=0.0013). (Table 3) The mean pulse rate was lower on Quadpill treatment (difference between group of −6.5 beats per minute (−10.6, −2.3).

TABLE 2

Effects on 24-hour mean SBP, by treatment period and sequence allocation (mmHg)

| Treatment sequence | Treatment period | | Within-individual difference: QuadPill-Placebo |
|---|---|---|---|
| | 1 | 2 | |
| QuadPill then Placebo | | | |
| Mean (SD) | −21.1 (6.8) | 5.3 (6.6) | −26.7 (9.2) |
| Sample size | 10 | 9 | 9 |
| Placebo then QuadPill | | | |
| Mean (SD) | −3.0 (17.9) | −16.4 (7.5) | −13.4 (22.9) |
| Sample size | 9 | 9 | 9 |
| Treatment effect | | | |
| Mean (SD) | | | −18.7 (2.1) & (95% CI-23.0; −14.3) |
| p-value | | | <.0001 |
| Sample size | | | 19 |

Paired t-test comparing ASBP at end of 4 week treatment period for QuadPill and Placebo shows significant reduction of 18.7 (p<0.0001).

SD=Standard deviation CI=Confidence interval

Treatment effect is estimated using a mixed regression model adjusted for baseline values.

TABLE 3

Effects of Quadpill and placebo on blood pressure parameters

| Parameter | QUADPILL TREATMENT PERIOD QUADPILL treatment period | | PLACEBO TREATMENT PERIOD Placebo treatment period | | Difference in change between | p-value * |
|---|---|---|---|---|---|---|
| | Baseline (week 0 or week 6) | End of treatment (week 4 or week 10) | Baseline (week 0 or week 6) | End of treatment (week 4 or week 10) | Quadpill and Placebo period in mmHg (95% CI) * | |
| | Mean BP levels (mmHg) | | | | | |
| Mean 24 hr SBP | 138.4 | 119.6 | 137.1 | 138.2 | −18.7 (−23.2; −14.2) | <0.0001 |
| Daytime ASBP | 141.7 | 121.4 | 140.3 | 143.7 | −22.3 (−26.9; −17.7) | <.0001 |

| Parameter | QUADPILL TREATMENT PERIOD QUADPILL treatment period | | PLACEBO TREATMENT PERIOD Placebo treatment period | | Difference in change between | p-value * |
|---|---|---|---|---|---|---|
| | Baseline (week 0 or week 6) | End of treatment (week 4 or week 10) | Baseline (week 0 or week 6) | End of treatment (week 4 or week 10) | Quadpill and Placebo period in mmHg (95% CI) * | |
| Daytime ADBP | 89.9 | 75.7 | 87.9 | 91.1 | −15.3 (−18.1; −12.6) | <.0001 |
| Night-time ASBP | 128.8 | 114.4 | 126.2 | 125.4 | −10.4 (−18.3; −2.6) | 0.0128 |
| Night-time ADBP | 77.7 | 66.8 | 77.8 | 79.4 | −12.5 (−17.1; −7.9) | <.0001 |
| Mean 24 hr DBP | 86.7 | 73.3 | 85.1 | 87.6 | −14.2 (−16.9; −11.5) | <.0001 |
| Office SBP | 149.9 | 122.1 | 145.8 | 144.6 | −22.4 (−28.3; −16.5) | <.0001 |
| Office DBP | 87.4 | 71.8 | 86.1 | 84.8 | −13.1 (−17.3; −8.8) | <.0001 |
| | | | | | Relative risk (95% CI) | |
| ABP < 135/ 85 mmHg | N/A | 15/18 (83.3%) | N/A | 7/18 (38.9%) | 2.14 (1.25; 3.65) | 0.0053 |

| Parameter | QUADPILL TREATMENT PERIOD QUADPILL treatment period | | PLACEBO TREATMENT PERIOD Placebo treatment period | | Difference in change between | p-value * |
|---|---|---|---|---|---|---|
| | Baseline (week 0 or week 6) | End of treatment (week 4 or week 10) | Baseline (week 0 or week 6) | End of treatment (week 4 or week 10) | Quadpill and Placebo period in mmHg (95% CI) * | |
| Office SBP < 140 and DBP < 90 mmHg | N/A | 18/18 (100.0%) | N/A | 6/18 (33.3%) | 3.01 (1.54; 5.89) | 0.0013 |

Neither the carryover effect (t=−0.17, p=0.868) or period effect (t=−1.05, p=0.308) were significant. There were no significant interactions by age, sex or BMI. In sensitivity analysis using a standard comparison (paired t-test), results were virtually identical with a difference in mean 24-hour SBP between the Quadpill and placebo periods of −18.7 mmHg, 95% CI −23.1; −14.2. Similarly in a second sensitivity analysis that included only patients with complete data (n=18) from both periods, results were also virtually identical with the difference in mean 24-hour SBP of −18.7, 95% CI −23.2; −14.2.

Compliance with therapy was high. The mean number of tablets missed in the last week was 0.2 (SD 0.4) for Quadpill and 0.3 (SD 0.6) for placebo. All 18 participants who finished the study completed the end-of-study acceptability questionnaire, with all reporting the study medication was either very easy (n=13) or easy (n=5) to swallow. In addition, all 18 participants reported it was either very likely (n=10) or likely (n=8) they would take the Quadpill if available commercially.

There were no serious adverse events. One patient reported dizziness while on the Quadpill causing temporary discontinuation of treatment; one patient reported vestibular dizziness during the washout period on placebo; and one patient reported urinary frequency in Quadpill and placebo phases (Table 4). Mean creatinine levels were higher at the end of the Quadpill than the placebo treatment periods: creatinine 78 mmol/L (SD 14) vs 71 (SD 14), p=0.02; as were urate levels: 0.4 (0.1) vs 0.3 (0.1), p=0.003. (Table 5) The absolute changes in creatinine (4.4, 95% CI 0.9-7.8)) and urate (0.03, 95% CI 0.001-0.04) were small, (no patient had more than a 12% increase in either variable) and appeared reversible (e.g. for those who received Quadpill first, the mean creatinine was x, y and z at baseline, 4 weeks and 10 weeks, respectively) There were no significant differences in ALT, AST, Sodium, potassium, total cholesterol or LDL-cholesterol.

100% of participants. This trial illustrates some of the potential advantages of an approach that uses multiple drugs at very low doses to achieve efficacy.

Small but statistically significant increases in creatinine and urate were observed in this trial, with no patient experiencing more than a 12% increase. The increase in creatinine may not be of clinical importance, as creatinine is affected not only by kidney function, but also by renal, especially glomerular, perfusion which can be reversibly reduced systemically or locally. Both approaches reduce the risk of kidney failure in people with increased intraglomerular pressure (manifested clinically as proteinuria), despite reversibly increasing creatinine levels. A creatinine effect of BP lowering is therefore to be expected, may not indicate long term renal harm, and could lead to renal benefit for the participants with raised intraglomerular pressure and proteinuria. The findings present for the first time placebo-controlled data that ultra-low dose multi-drug combination therapy can be very effective in BP lowering, even for previously untreated patients with very mildly elevated

TABLE 4

Adverse events

| Event | Study drug allocated when occurred | Treatment period when occurred | Severity | Action Taken | Outcome | Relationship |
|---|---|---|---|---|---|---|
| Gastro Illness | Quadpill | $1^{st}$ | Mild | None | Resolved | Not Related |
| Headache | Quadpill | $1^{st}$ | Mild | None | Resolved | Not Related |
| Dry Nose | Placebo | $2^{nd}$ | Mild | None | Resolved | Not Related |
| Dizziness (Vestibular) | Neither | Between $1^{st}$ & $2^{nd}$ | Mild | None | Resolved | Not Related |
| Dizziness | Quadpill | 1st | Mild | Temporarily discontinued study drug | Resolved | Related |
| Urine Frequency* | Quadpill | $1^{st}$ | Mild | None | Resolved | Possibly related |
| Urine Frequency* | Placebo | $2^{nd}$ | Mild | None | Resolved | Possibly Related |
| Respiratory Tract Infection | Quadpill | $2^{nd}$ | Mild | None | Resolved | Not Related |

*Urine Frequency was reported by one male patient during the intervention phase and same patient in the placebo phase. He was instructed to consult local doctor for urologic assessment.

TABLE 5

Biochemical

| | QuadPill at end of 4 weeks | Placebo at end of 4 weeks | Difference at 4 weeks (95% CI) | p-value* |
|---|---|---|---|---|
| Creatinine (μmol/L) | 78.2 | 70.9 | 4.4 (0.9; 7.8)) | 0.0165 |
| ALT (μmol/L) | 33.2 | 30.4 | 3.1 (−4.3; 10.5) | 0.38 |
| AST (μmol/L) | 27.2 | 33.8 | −7.3 (−24.1; 9.5) | 0.37 |
| Sodium (mmol/L) | 139.9 | 140.5 | −0.6 (−1.8; 0.6) | 0.32 |
| Potassium (mmol/L) | 4.4 | 4.5 | −0.04 (−0.2; 0.1) | 0.62 |
| Urate (mmol/L) | 0.4 | 0.3 | 0.03 (0.01; 0.04) | 0.0030 |
| Total Cholesterol | 5.9 | 5.8 | 0.2 (−0.2; 0.6) | 0.27 |
| LDL Cholesterol (mmol/L) | 3.5 | 3.5 | 0.2 (−0.2; 0.5) | 0.31 |

Discussion

This study found that a Quadpill—a capsule containing four BP lowering components—reduced 24 hr ambulatory SBP by 18 mmHg and achieved office BP<140/90 mmHg in blood pressure levels. This justifies further trials on long-term efficacy and safety, both for initial treatment and among patients with inadequate control and/or side effects while receiving monotherapy.

Example 2: Comparative Study of Quadruple Combination Versus Standard Dose Monotherapy for the Treatment of Hypertension Objectives The primary objective of this study is to investigate in a double blind randomized controlled trial whether initiating treatment with a quadruple combination therapy will lower blood pressure more effectively, and with fewer side effects, compared to initiating standard dose monotherapy as per current guidelines in patients with hypertension. The secondary objective is to assess if this approach is safe and has fewer side effects compared to standard care.

Study Design

This will be a 12-week double blind randomized controlled trial (1:1) of 650 patients with grade 1 and 2 essential hypertension. Subjects will be randomized through a central computer-based randomization service, to initial therapy with the quadruple combination composition or to an angiotensin receptor blocker (ARB), with option to add a calcium channel blocker (CCB) as required, as per current Australian Hypertension guidelines. The primary outcome will be reduction in mean systolic blood pressure using standardized automated BP cuff at 12 weeks. Secondary outcomes will include: proportion with controlled blood pressure at 6 weeks, 12 weeks, ambulatory blood pressure (ABP) measures and tolerability/occurrence of adverse events.

Eligibility Criteria

The inclusion criteria are as follows:

Adults (≥18 years)

Treatment naïve, or currently not on treatment (not taken in last 4 weeks), or taking one BP lowering drug (angiotensin converting enzyme inhibitor, angiotensin receptor blocker, calcium channel blocker, beta-blocker, aldosterone antagonist, alpha-blocker)

SBP 140-179 mmHg and/or DBP 90-109 mmHg documented on two occasions more than a week apart At least one of the measures should be documented by study staff with study automatic BP device OR recorded as daytime average SBP ≥135 mmHg and/or DBP ≥85 mmHg on 24 hour ambulatory BP monitoring At least one of these measures should be recent (in last 12 weeks)

24 hour Ambulatory BP monitoring daytime average SBP ≥135 mmHg and/or DBP ≥85 mmHg—documented within 12 weeks of randomization The exclusion criteria are as follows:

Contraindication to irbesartan, amlodipine, indapamide or bisoprolol

Evidence of secondary cause of hypertension e.g. renal artery stenosis; Significant renal impairment (eGRF <50), raised serum potassium (above lab normal limit)

Women who are pregnant, breast feeding and/or of child-bearing potential and not using medically acceptable form of contraception throughout the study (pharmacological or barrier methods)

Concomitant illness, physical impairment or mental condition which in the opinion of the study team/primary care physician could interfere with the conduct of the study including outcome assessments Participation in a concurrent interventional medical investigation or clinical trial. Patients in observational, natural history and/or epidemiological studies not involving an intervention are eligible.

Participants responsible primary care or other responsible physician believes it is not appropriate for participant to switch current monotherapy Inability or unwillingness to provide written informed consent Unable to complete study procedures including 24 hour Ambulatory BP Definite indication for combination therapy Study Treatment Patients who meet criteria for inclusion will be randomized to: 1) A combination pill comprising the following four components—irbesartan (37.5 mg), amlodipine besylate (1.25 mg), indapamide (0.625 mg), bisoprolol fumarate (2.5 mg); or 2) irbesartan (150 mg).

Patients who are currently on monotherapy will be asked to stop their treatment while they are taking the study treatment. At 6 weeks if the BP is greater than 140/90 mmHg in either arm amlodipine besylate (5 mg) will be added by study staff.

Outcomes

The primary outcome will be the difference between groups in mean automated office systolic blood pressure at 12 weeks adjusted for baseline values.

The secondary outcomes include the following:

The 24-hour ambulatory blood pressure measures
  a. Difference between groups in mean 24-hour SBP and DBP at 12 weeks
  b. Difference between groups in mean change in 24-hour SBP and DBP from 0 to 12 weeks
  c. Difference between groups in mean daytime SBP and DBP at 12 weeks Difference between groups in mean night-time SBP and DBP at 12 weeks
  d. Difference between groups in daytime, night-time, and 24 hour BP load (percentage area under the blood pressure curve above normal day, night, and 24 hour values as per NHFA Guide to management of hypertension 2008)
  e. Difference between groups in the proportion of non-dippers (night-time BP is not more than 10%/lower than average daytime BP as per NHFA Guide to management of hypertension 2008) and coefficient of variability of BP (O'Brien, E., G. Parati, and G. Stergiou, Hypertension, 2013. 62(6): p. 988-94).

Other blood pressure measures in the quadruple group vs control groups:
  a. Change in mean diastolic blood pressure from baseline to 12 weeks,
  b. Hypertension control (% with SBP <140 mmHg and DBP <90 mmHg) at 6 and 12 weeks,
  c. Percentage requiring step-up treatment at 6 weeks
  d. Percentage with both BP control (as defined above) and no adverse events.
  e. Difference between groups in SBP and DBP variability Tolerability
  a. Difference between groups in potentially related side-effects (dizziness, blurred vision, syncope/collapse/fall, chest pain/angina, shortness of breath, cough, wheeze, ankle oedema, skin rash, itching, gout, hyperkalaemia, hypokalaemia, hyponatraemia, other)
  b. Difference between groups in mean potassium, uric acid, blood glucose, cholesterol and fractions, ALT, AST, UACR (Urine albumin-to-creatinine ratio) and creatinine levels.
  c. Difference between groups in participant withdrawals from treatment Statistical Methods All analyses of study outcomes will be conducted according to the principle of intention-to-treat. The primary analysis of change in systolic blood pressure (SBP) at 12 weeks will be performed using an analysis of covariance (ANCOVA) including the treatment arm and baseline SBP as a covariate. Continuous secondary outcomes will be analyzed similarly. Additional analyses will include both 6-week and 12-week measurements in a longitudinal model including treatment arm, visit, and treatment by visit interaction as well as the baseline measurement. Within-patient correlations will be modelled using generalized estimating equations. A similar approach will be applied to binary endpoints (e.g. hypertension control) with log-binomial regression used in place of linear regression. There will also be pre-defined subgroup analyses, including by baseline blood pressure, gender, age and hypertension treatment history. A detailed analysis plan will be developed prior to unblinding.

Example 3: Pharmaceutical Compositions

The following pharmaceutical compositions are prepared with the specified components and doses as shown in the following Table.

| Agent | Proposed Dose (mg) | Proposed Dose Range (mg) |
|---|---|---|
| Composition 1 | | |
| Amlodipine besylate | 1.25 | 1-1.5 |
| Atenolol | 12.5 | 10-15 |
| Hydrochlorothiazide | 6.25 | 5-7.5 |
| Telmisartan | 10 | 8-12 |
| Composition 2 | | |
| Amlodipine besylate | 1.25 | 1-1.5 |
| Bisoprolol Fumarate | 2.5 | 2-3 |
| Indapamide | 0.625 | 0.5-0.75 |
| Telmisartan | 10 | 8-12 |
| Composition 3 | | |
| Amlodipine besylate | 1.25 | 1-1.5 |
| Bisoprolol Fumarate | 2.5 | 2-3 |
| Chlorthalidone | 12.5 | 10-15 |
| Telmisartan | 10 | 8-12 |
| Composition 4 | | |
| Amlodipine besylate | 1.25 | 1-1.5 |
| Atenolol | 12.5 | 10-15 |
| Chlorthalidone | 12.5 | 10-15 |
| Telmisartan | 10 | 8-12 |
| Composition 5 | | |
| Amlodipine besylate | 1.25 | 1-1.5 |
| Bisoprolol Fumarate | 2.5 | 2-3 |
| Chlorthalidone | 12.5 | 10-15 |
| Irbesartan | 37.5 | 30-45 |
| Composition 6 | | |
| Amlodipine besylate | 1.25 | 1-1.5 |
| Atenolol | 12.5 | 10-15 |
| Chlorthalidone | 12.5 | 10-15 |
| Irbesartan | 37.5 | 30-45 |

EMBODIMENTS

Embodiment 1

A pharmaceutical composition comprising
(a) an angiotensin II receptor blocker;
(b) a diuretic;
(c) a calcium channel blocker; and
(d) a beta-blocker;
wherein the dose of each (a), (b), (c), and (d) is from about 20% to about 60% of the lowest hypertension therapeutic dose (LHTD) for each of the (a), (b), (c), and (d).

Embodiment 2

The pharmaceutical composition of embodiment 1, wherein the dose of each (a), (b), (c), and (d) is from about 40% to about 60% of the lowest hypertension therapeutic dose (LHTD) for each of the (a), (b), (c), and (d).

Embodiment 3

The pharmaceutical composition of embodiments 1 or 2, wherein the pharmaceutical composition is essentially free of a lipid-regulating agent, platelet function altering agent, a serum homocysteine lowering agent, or a combination thereof.

Embodiment 4

The pharmaceutical composition of embodiment 3, wherein the pharmaceutical composition is essentially free of a lipid-regulating agent.

Embodiment 5

The pharmaceutical composition of embodiment 4, wherein the lipid-regulating agent is atorvastatin, simvastatin, cerivastatin, fluvastatin, or pravastatin.

Embodiment 6

The pharmaceutical composition of embodiments 4 or 5, wherein the lipid-regulating agent is atorvastatin or simvastatin.

Embodiment 7

The pharmaceutical composition of embodiment 3, wherein the pharmaceutical composition is essentially free of a platelet function altering agent.

Embodiment 8

The pharmaceutical composition of embodiment 7, wherein the platelet function altering agent is aspirin, ticlopidine, dipyridamole, clopidogrel, abciximab, or ibuprofen.

Embodiment 9

The pharmaceutical composition of embodiments 7 or 8, wherein the platelet function altering agent is aspirin.

Embodiment 10

The pharmaceutical composition of embodiment 3, wherein the pharmaceutical composition is essentially free of a serum homocysteine lowering agent.

Embodiment 11

The pharmaceutical composition of embodiment 10, wherein the serum homocysteine lowering agent is folic acid, vitamin B6, vitamin B12, or a combination thereof.

Embodiment 12

The pharmaceutical composition of embodiments 10 or 11, wherein the serum homocysteine lowering agent is folic acid.

Embodiment 13

The pharmaceutical composition of any one of embodiments 1-12, wherein the diuretic is a thiazide diuretic.

Embodiment 14

The pharmaceutical composition of embodiment 13, wherein the dose of the thiazide diuretic is about 50% of the lowest hypertension therapeutic dose (LHTD) for the thiazide diuretic.

Embodiment 15

The pharmaceutical composition of embodiments 13 or 14, wherein the thiazide diuretic is altizide, bendroflumethiazide, chlorothiazide, cyclopenthiazide, cyclothiazide, epitizide, hydrochlorothiazide, hydroflumethiazide, mebutizide, methyclothiazide, polythiazide, trichlormethiazide, or the pharmaceutically acceptable salt or hydrate thereof.

Embodiment 16

The pharmaceutical composition of any one of embodiments 13-15, wherein the thiazide diuretic is hydrochlorothiazide.

Embodiment 17

The pharmaceutical composition of embodiment 16, wherein the dose of the hydrochlorothiazide is about 6.25 mg.

Embodiment 18

The pharmaceutical composition of any one of embodiments 1-12, wherein the diuretic is a thiazide-like diuretic.

Embodiment 19

The pharmaceutical composition of embodiment 18, wherein the dose of the thiazide-like diuretic is about 50% of the lowest hypertension therapeutic dose (LHTD) for the thiazide-like diuretic.

Embodiment 20

The pharmaceutical composition of embodiments 18 or 19, wherein the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof.

Embodiment 21

The pharmaceutical composition of any one of embodiments 18-20, wherein the thiazide-like diuretic is indapamide or the hydrate thereof.

Embodiment 22

The pharmaceutical composition of embodiment 21, wherein the thiazide-like diuretic is indapamide.

Embodiment 23

The pharmaceutical composition of embodiment 22, wherein the dose of the indapamide is about 0.625 mg.

Embodiment 24

The pharmaceutical composition of any one of embodiments 18-20, wherein the thiazide-like diuretic is chlorthalidone.

Embodiment 25

The pharmaceutical composition of embodiment 24, wherein the dose of the chlorthalidone is about 12.5 mg.

Embodiment 26

The pharmaceutical composition of any one of embodiments 1-12, wherein the diuretic is a loop diuretic.

Embodiment 27

The pharmaceutical composition of embodiment 26, wherein the dose of the loop diuretic is about 50% of the lowest hypertension therapeutic dose (LHTD) for the loop-diuretic.

Embodiment 28

The pharmaceutical composition of embodiments 26 or 27, wherein the loop diuretic is furosemide, bumetanide, etacrynic acid, etozolin, muzolimine, ozolinone, piretanide, tienilic acid, torasemide, or the pharmaceutically acceptable salt or hydrate thereof.

Embodiment 29

The pharmaceutical composition of any one of embodiments 1-12, wherein the diuretic is dichlorphenamide, amiloride, pamabrom, mannitol, acetazolamide, methazolamide, spironolactone, triamterene, or the pharmaceutically acceptable salt or hydrate thereof.

Embodiment 30

The pharmaceutical composition of embodiment 29, wherein the dose of the diuretic is about 50% of the lowest hypertension therapeutic dose (LHTD) for the diuretic.

Embodiment 31

The pharmaceutical composition of any one of embodiments 1-30, wherein the dose of the calcium channel blocker is about 50% of the lowest hypertension therapeutic dose (LHTD) for the calcium channel blocker.

Embodiment 32

The pharmaceutical composition of embodiment 31, wherein the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof.

Embodiment 33

The pharmaceutical composition of embodiments 31 or 32, wherein the calcium channel blocker is amlodipine or the pharmaceutically acceptable salt thereof.

Embodiment 34

The pharmaceutical composition of embodiment 33, wherein the calcium channel blocker is amlodipine besylate.

Embodiment 35

The pharmaceutical composition of embodiment 34, wherein the dose of amlodipine besylate is about 1.25 mg.

Embodiment 36

The pharmaceutical composition of any one of embodiments 1-35, wherein the dose of the beta-blocker is about 50% of the lowest hypertension therapeutic dose (LHTD) for the beta-blocker.

Embodiment 37

The pharmaceutical composition of embodiment 36, wherein the beta-blocker is acebutolol, atenolol, betaxolol, bisoprolol, carteolol, esmolol, penbutolol, metoprolol, nadolol, nebivolol, pindolol, sotalol, propranolol, carvedilol, labetalol, timolol, esmolol, celiprolol, oxprenolol, levobunolol, practolol, metipranolol, landiolol, bopindolol, pronethalol, butaxamine, bevantolol, tertatolol, arotinolol, levobetaxolol, befunolol, amosulalol, tilisolol, or the pharmaceutically acceptable salt or hydrate thereof.

Embodiment 38

The pharmaceutical composition of embodiments 36 or 37, wherein the beta-blocker is atenolol.

Embodiment 39

The pharmaceutical composition of embodiment 38, wherein the dose of atenolol is about 12.5 mg.

Embodiment 40

The pharmaceutical composition of embodiments 36 or 37, wherein the beta-blocker is bisoprolol or the pharmaceutically acceptable salt thereof.

Embodiment 41

The pharmaceutical composition of embodiment 40, wherein the beta-blocker is bisoprolol fumarate.

Embodiment 42

The pharmaceutical composition of embodiment 41, wherein the dose of bisoprolol fumarate is about 2.5 mg.

Embodiment 43

The pharmaceutical composition of any one of embodiments 1-42, wherein the dose of the angiotensin II receptor blocker is about 50% of the lowest hypertension therapeutic dose (LHTD) for the angiotensin II receptor blocker.

Embodiment 44

The pharmaceutical composition of any one of embodiments 1-43, wherein the angiotensin II receptor blocker is irbesartan, telmisartan, valsartan, candesartan, eprosartan, olmesartan, azilsartan, losartan, or the pharmaceutically acceptable salt or hydrate thereof.

Embodiment 45

The pharmaceutical composition of embodiments 43 or 44, wherein the angiotensin II receptor blocker is irbesartan.

Embodiment 46

The pharmaceutical composition of embodiment 45, wherein the dose of the irbesartan is about 37.5 mg.

Embodiment 47

The pharmaceutical composition of embodiments 43 or 44, wherein the angiotensin II receptor blocker is telmisartan.

Embodiment 48

The pharmaceutical composition of embodiment 47, wherein the dose of the telmisartan is about 10 mg.

Embodiment 49

The pharmaceutical composition of embodiment 1, wherein the angiotensin II receptor blocker is irbesartan, the diuretic is hydrochlorothiazide, the calcium channel blocker is amlodipine besylate, and the beta blocker is atenolol.

Embodiment 50

The pharmaceutical composition of embodiment 49, wherein the dose of irbesartan is about 30 mg to about 45 mg, the dose of hydrochlorothiazide is about 5 mg to about 7.5 mg, the dose of amlodipine besylate is about 1 mg to about 1.5 mg, and the dose of atenolol is about 10 mg to about 15 mg.

Embodiment 51

The pharmaceutical composition of embodiment 49, wherein the dose of irbesartan is about 37.5 mg, the dose of hydrochlorothiazide is about 6.25 mg, the dose of amlodipine besylate is about 1.25 mg, and the dose of atenolol is about 12.5 mg.

Embodiment 52

The pharmaceutical composition of embodiment 1, wherein the angiotensin II receptor blocker is telmisartan, the diuretic is hydrochlorothiazide, the calcium channel blocker is amlodipine besylate, and the beta blocker is atenolol.

Embodiment 53

The pharmaceutical composition of embodiment 52, wherein the dose of telmisartan is about 8 mg to about 12 mg, the dose of hydrochlorothiazide is about 5 mg to about 7.5 mg, the dose of amlodipine besylate is about 1 mg to about 1.5 mg, and the dose of atenolol is about 10 mg to about 15 mg.

Embodiment 54

The pharmaceutical composition of embodiment 52, wherein the dose of telmisartan is about 10 mg, the dose of hydrochlorothiazide is about 6.25 mg, the dose of amlodipine besylate is about 1.25 mg, and the dose of atenolol is about 12.5 mg.

Embodiment 55

The pharmaceutical composition of embodiment 1, wherein the angiotensin II receptor blocker is irbesartan, the diuretic is indapamide, the calcium channel blocker is amlodipine besylate, and the beta-blocker is bisoprolol fumarate.

Embodiment 56

The pharmaceutical composition of embodiment 55, wherein the dose of irbesartan is about 30 mg to about 45 mg, the dose of indapamide is about 0.5 mg to about 0.75 mg, the dose of amlodipine besylate is about 1 mg to about 1.5 mg, and the dose of bisoprolol fumarate is about 2 mg to about 3 mg.

Embodiment 57

The pharmaceutical composition of embodiment 55, wherein the dose of irbesartan is about 37.5 mg, the dose of indapamide is about 0.625 mg, the dose of amlodipine is about 1.25 mg, and the dose of bisoprolol fumarate is about 2.5 mg.

Embodiment 58

The pharmaceutical composition of embodiment 1, wherein the angiotensin II receptor blocker is telmisartan, the diuretic is indapamide, the calcium channel blocker is amlodipine besylate, and the beta-blocker is bisoprolol fumarate.

Embodiment 59

The pharmaceutical composition of embodiment 58, wherein the dose of telmisartan is about 8 mg to about 12 mg, the dose of indapamide is about 0.5 mg to about 0.75 mg, the dose of amlodipine besylate is about 1 mg to about 1.5 mg, and the dose of bisoprolol fumarate is about 2 mg to about 3 mg.

Embodiment 60

The pharmaceutical composition of embodiment 58, wherein the dose of telmisartan is about 10 mg, the dose of indapamide is about 0.625 mg, the dose of amlodipine besylate is about 1.25 mg, and the dose of bisoprolol fumarate is about 2.5 mg.

Embodiment 61

The pharmaceutical composition of embodiment 1, wherein the angiotensin II receptor blocker is telmisartan, the diuretic is chlorthalidone, the calcium channel blocker is amlodipine besylate, and the beta-blocker is bisoprolol fumarate.

Embodiment 62

The pharmaceutical composition of embodiment 61, wherein the dose of telmisartan is about 8 mg to about 12 mg, the dose of chlorthalidone is about 10 mg to about 15 mg, the dose of amlodipine besylate is about 1 mg to about 1.5 mg, and the dose of bisoprolol fumarate is about 2 mg to about 3 mg.

Embodiment 63

The pharmaceutical composition of embodiment 61, wherein the dose of telmisartan is about 10 mg, the dose of chlorthalidone is about 12.5 mg, the dose of amlodipine besylate is about 1.25 mg, and the dose of bisoprolol fumarate is about 2.5 mg.

Embodiment 64

The pharmaceutical composition of embodiment 1, wherein the angiotensin II receptor blocker is telmisartan, the diuretic is chlorthalidone, the calcium channel blocker is amlodipine besylate, and the beta-blocker is atenolol.

Embodiment 65

The pharmaceutical composition of embodiment 64, wherein the dose of telmisartan is about 8 mg to about 12 mg, the dose of chlorthalidone is about 10 mg to about 15 mg, the dose of amlodipine besylate is about 1 mg to about 1.5 mg, and the dose of atenolol is about 10 mg to about 15 mg.

Embodiment 66

The pharmaceutical composition of embodiment 64, wherein the dose of telmisartan is about 10 mg, the dose of chlorthalidone is about 12.5 mg, the dose of amlodipine besylate is about 1.25 mg, and the dose of atenolol is about 12.5 mg.

Embodiment 67

The pharmaceutical composition of embodiment 1, wherein the angiotensin II receptor blocker is irbesartan, the diuretic is chlorthalidone, the calcium channel blocker is amlodipine besylate, and the beta-blocker is bisoprolol fumarate.

Embodiment 68

The pharmaceutical composition of embodiment 67, wherein the dose of irbesartan is about 30 mg to about 45 mg, the dose of chlorthalidone is about 10 mg to about 15 mg, the dose of amlodipine besylate is about 1 mg to about 1.5 mg, and the dose of bisoprolol fumarate is about 2 mg to about 3 mg.

Embodiment 69

The pharmaceutical composition of embodiment 67, wherein the dose of irbesartan is about 37.5 mg, the dose of chlorthalidone is about 12.5 mg, the dose of amlodipine besylate is about 1.25 mg, and the dose of bisoprolol fumarate is about 2.5 mg.

Embodiment 70

The pharmaceutical composition of embodiment 1, wherein the angiotensin II receptor blocker is irbesartan, the diuretic is chlorthalidone, the calcium channel blocker is amlodipine besylate, and the beta-blocker is atenolol.

Embodiment 71

The pharmaceutical composition of embodiment 70, wherein the dose of irbesartan is about 30 mg to about 45 mg, the dose of chlorthalidone is about 10 mg to about 15 mg, the dose of amlodipine besylate is about 1 mg to about 1.5 mg, and the dose of atenolol is about 10 mg to about 15 mg.

Embodiment 72

The pharmaceutical composition of embodiment 70, wherein the dose of irbesartan is about 37.5 mg, the dose of chlorthalidone is about 12.5 mg, the dose of amlodipine besylate is about 1.25 mg, and the dose of atenolol is about 12.5 mg.

Embodiment 73

The pharmaceutical composition of any one of embodiments 1-72, wherein (a), (b), (c) and (d) are provided in one formulation.

Embodiment 74

The pharmaceutical composition of any one of embodiments 1-72, wherein (a), (b), (c) and (d) are each provided in a separate formulation.

Embodiment 75

The pharmaceutical composition of any one of embodiments 1-72, wherein two of the (a), (b), (c) and (d) are provided in one formulation.

Embodiment 76

The pharmaceutical composition of any one of embodiments 1-72, wherein three of the (a), (b), (c) and (d) are provided in one formulation.

Embodiment 77

The pharmaceutical composition of any one of embodiments 1-76, wherein the pharmaceutical composition is in the form of pill, tablet or capsule.

Embodiment 78

The pharmaceutical composition of any one of embodiments 1-77, wherein the pharmaceutical composition is suitable for oral administration.

Embodiment 79

A method of treating hypertension in a subject in need thereof comprising administering the pharmaceutical composition of any one of embodiments 1-78.

Embodiment 80

The method of embodiment 79, wherein the treatment results in a systolic blood pressure (SBP) of less than about 140 mmHg.

Embodiment 81

The method of embodiments 79 or 80, wherein the treatment results in a reduction of systolic blood pressure (SBP) of about 10 mmHg or greater.

Embodiment 82

The method of any one of embodiments 79-81, wherein the treatment results in a diastolic blood pressure (DBP) of less than about 90 mmHg.

Embodiment 83

The method of any one of embodiment 79-82, wherein the treatment results in a reduction of diastolic blood pressure (DBP) of about 5 mmHg or greater.

Embodiment 84

The method of any one of embodiments 79-83, wherein treatment results in a reduction in systolic blood pressure (SBP) that is greater than the reduction obtained with the full lowest hypertension therapeutic dose of any one of the (a), (b), (c), and (d) in the pharmaceutical composition.

Embodiment 85

The method of any one of embodiments 79-84, wherein treatment results in a reduction in diastolic blood pressure (DBP) that is greater than the reduction obtained with the full lowest hypertension therapeutic dose of any one of (a), (b), (c), and (d) in the pharmaceutical composition.

Embodiment 86

The method of any one of embodiments 79-85, wherein the treatment results in greater long term tolerability and reduced risk of side effects when compared to treatment with the full lowest hypertension therapeutic dose of any one of (a), (b), (c), and (d) in the pharmaceutical composition.

Embodiment 87

The method of any one of embodiments 79-83, wherein treatment results in a reduction in systolic blood pressure (SBP) that is greater than or equal to the reduction obtained with the combination of any two of the (a), (b), (c), and (d) in the pharmaceutical composition, wherein the dose of each (a), (b), (c), and (d) is about 50% of the lowest hypertension therapeutic dose.

Embodiment 88

The method of any one of embodiments 79-84, wherein treatment results in a reduction in diastolic blood pressure (DBP) that is greater than or equal to the reduction obtained with a combination of any two of the (a), (b), (c), and (d) in the pharmaceutical composition, wherein the dose of each (a), (b), (c), and (d) is about 50% of the lowest hypertension therapeutic dose.

Embodiment 89

The method of any one of embodiments 79-85, wherein the treatment results in greater long term tolerability and reduced risk of side effects when compared to treatment with a combination of any two of (a), (b), (c), and (d) in the pharmaceutical composition, wherein the dose of each (a), (b), (c), and (d) is about 50% of the lowest hypertension therapeutic dose.

Embodiment 90

The method of any one of embodiments 79-89, wherein the treatment is the initial or first-line treatment of hypertension.

Embodiment 91

The method of any one of the embodiments 79-90, wherein the subject is not receiving any previous hypertension therapy prior to treatment.

Embodiment 92

A pharmaceutical composition consisting essentially of
(a) an angiotensin II receptor blocker;
(b) a diuretic;
(c) a calcium channel blocker; and
(d) a beta-blocker;
wherein the dose of each (a), (b), (c), and (d) is from about 20% to about 60% of the lowest hypertension therapeutic dose (LHTD) for each of the (a), (b), (c), and (d).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A pharmaceutical composition comprising
(a) irbesartan;
(b) hydrochlorothiazide;
(c) amlodipine besylate; and
(d) atenolol;
wherein the dose of irbesartan is about 37.5 mg, the dose of hydrochlorothiazide is about 6.25 mg, the dose of amlodipine besylate is about 1.25 mg, and the dose of atenolol is about 12.5 mg, wherein (a), (b), (c) and (d) are provided in one formulation.

2. The pharmaceutical composition of claim 1, wherein the pharmaceutical composition is essentially free of a lipid-regulating agent, platelet function altering agent, a serum homocysteine lowering agent, or a combination thereof.

3. The pharmaceutical composition of claim 1, wherein the pharmaceutical composition is suitable for oral administration.

4. A method of treating hypertension in a subject in need thereof comprising administering the pharmaceutical composition comprising:
(a) irbesartan;
(b) hydrochlorothiazide;
(c) amlodipine besylate; and
(d) atenolol;
wherein the dose of irbesartan is about 37.5 mg, the dose of hydrochlorothiazide is about 6.25 mg, the dose of amlodipine besylate is about 1.25 mg, and the dose of atenolol is about 12.5 mg, wherein (a), (b), (c) and (d) are provided in one formulation.

5. The method of claim 4, wherein the treatment results in a reduction of systolic blood pressure (SBP) of about 10 mmHg or greater.

6. The method of claim 4, wherein the treatment results in a reduction of diastolic blood pressure (DBP) of about 5 mmHg or greater.

* * * * *